United States Patent
Reves et al.

(10) Patent No.: US 11,464,888 B2
(45) Date of Patent: *Oct. 11, 2022

(54) MOLDABLE FORMULATIONS CONTAINING AN OXYSTEROL IN AN ACELLULAR TISSUE MATRIX

(71) Applicant: Warsaw Orthopedic, Inc., Warsaw, IN (US)

(72) Inventors: Benjamin T. Reves, Germantown, TN (US); Roger E. Harrington, Collierville, TN (US); Jerbrena C. Jacobs, Hernando, MS (US); David S. Scher, Collierville, TN (US); Daniel A. Shimko, Germantown, TN (US)

(73) Assignee: Warsaw Orthopedic, Inc., Warsaw, IN (US)

(*) Notice: Subject to any disclaimer, the term of this patent is extended or adjusted under 35 U.S.C. 154(b) by 0 days.

This patent is subject to a terminal disclaimer.

(21) Appl. No.: 15/620,189

(22) Filed: Jun. 12, 2017

(65) Prior Publication Data

US 2018/0353654 A1   Dec. 13, 2018

(51) Int. Cl.
*A61L 27/54*   (2006.01)
*A61L 27/44*   (2006.01)
*A61L 27/36*   (2006.01)

(52) U.S. Cl.
CPC .......... *A61L 27/54* (2013.01); *A61L 27/3608* (2013.01); *A61L 27/3633* (2013.01); *A61L 27/44* (2013.01); *A61L 2300/222* (2013.01); *A61L 2300/412* (2013.01); *A61L 2400/06* (2013.01); *A61L 2430/02* (2013.01)

(58) Field of Classification Search
None
See application file for complete search history.

(56) References Cited

U.S. PATENT DOCUMENTS

| | | | |
|---|---|---|---|
| 4,877,864 A | 10/1989 | Wang et al. | |
| 4,891,359 A | 1/1990 | Saferstein et al. | |
| 5,336,616 A | 8/1994 | Livesey et al. | |
| 5,397,353 A | 3/1995 | Oliver et al. | |
| 5,683,459 A | 11/1997 | Brekke | |
| 5,899,939 A | 5/1999 | Boyce et al. | |
| 6,371,992 B1 * | 4/2002 | Tanagho | A61K 35/22 424/423 |
| 6,432,710 B1 | 8/2002 | Boss, Jr. et al. | |
| 6,936,271 B1 | 8/2005 | Oliver et al. | |
| 7,638,129 B2 | 12/2009 | Kawai et al. | |
| 7,897,588 B2 | 3/2011 | Parhami | |
| 8,022,052 B2 | 9/2011 | Parhami et al. | |
| 8,268,008 B2 | 9/2012 | Betz et al. | |
| 8,475,824 B2 | 7/2013 | McKay | |
| 8,586,070 B2 | 11/2013 | Briest | |
| 8,642,065 B2 | 2/2014 | Hans Moore et al. | |
| 8,758,791 B2 | 6/2014 | McKay | |
| 8,877,221 B2 | 11/2014 | McKay | |
| 8,900,617 B2 | 12/2014 | McKay | |
| 9,271,821 B2 * | 3/2016 | Roock | A61F 2/02 |
| 9,877,836 B2 * | 1/2018 | Reves | A61F 2/2846 |
| 9,878,070 B2 * | 1/2018 | Reves | A61L 27/46 |
| 2003/0009235 A1 | 1/2003 | Manrique et al. | |
| 2006/0251735 A1 | 11/2006 | Parhami | |
| 2006/0270645 A1 | 11/2006 | Parhami | |
| 2007/0248575 A1 | 10/2007 | Connor et al. | |
| 2009/0202660 A1 | 8/2009 | Parhami | |
| 2009/0220562 A1 | 9/2009 | Parhami | |
| 2010/0034781 A1 | 2/2010 | Parhami et al. | |
| 2010/0112030 A1 | 5/2010 | Parhami et al. | |
| 2010/0119492 A1 | 5/2010 | Hans et al. | |
| 2010/0137903 A1 | 6/2010 | Lee et al. | |
| 2010/0256774 A1 * | 10/2010 | Wang | A61L 27/3608 623/23.63 |
| 2011/0008297 A1 | 1/2011 | Parhami et al. | |
| 2011/0104230 A1 | 5/2011 | Mousa et al. | |
| 2011/0276147 A1 | 11/2011 | Cook et al. | |
| 2012/0107401 A1 | 5/2012 | McKay | |
| 2012/0195952 A1 | 8/2012 | King | |
| 2012/0219599 A1 | 8/2012 | Moore et al. | |

(Continued)

FOREIGN PATENT DOCUMENTS

CN  105636598 A  6/2016
EP  1112096 B1  3/2003

(Continued)

OTHER PUBLICATIONS

Buser, Z., et al., Eur Spine J 26: 2763-2772 (May 25, 2017). (Year: 2017).*
Stappenbeck, F., et al., Bioorganic & Medicinal Chemistry Letters 22: 5893-5897 (2012). (Year: 2012).*
Stappenbeck, Frank, et al. Novel oxysterols activate the Hedgehog pathway and induce osteogenesis. Bioorganic & Medicinal Chemistry Letters, vol. 22, pp. 5893-5897, 2012 Elsevier Ltd., 5 pages.
International Search Report and Written Opinion of the ISA/US dated Apr. 8, 2016 of PCT/US2015/064526 filed Dec. 8, 2015.
Nedelcu, et al. Oxysterol binding to the extracellular domain of Smoothened in Hedgehog Signaling. Nature Chemical Biology 9(9): 557-564 (2013) Supplementary information pp. 1-28, retrieved from internet Mar. 9, 2016 from URL: http://www.nature.com/nchembio/journal/v9/n9/extref/nchembio.1290-S1.pdf, entire document.

(Continued)

*Primary Examiner* — David J Blanchard
*Assistant Examiner* — Daniel F Coughlin
(74) *Attorney, Agent, or Firm* — Sorell, Lenna & Schmidt, LLP; William D. Schmidt, Esq.

(57) ABSTRACT

Provided is an implant configured to fit at or near a bone defect to promote bone growth. The implant comprises an oxysterol uniformly disposed in an acellular tissue matrix (ATM). The acellular tissue matrix can be porcine collagen, which in some cases is crosslinked. The implant can contain an acellular porcine crosslinked collagen in an amount of about 5 wt. % to about 25 wt. % of the implant and an oxysterol in an amount of about 5 wt. % to about 90 wt. % of the implant. The oxysterol can be Oxy133 monohydrate or an Oxy133 polymorph. Methods of making and using the implant are further provided.

15 Claims, 6 Drawing Sheets

(56) References Cited

U.S. PATENT DOCUMENTS

| | | | |
|---|---|---|---|
| 2012/0265167 A1 | 10/2012 | Simonson et al. | |
| 2013/0045923 A1 | 2/2013 | Armitage et al. | |
| 2013/0244942 A1 | 9/2013 | Benedict et al. | |
| 2013/0267465 A1 | 10/2013 | Armitage et al. | |
| 2014/0170202 A1 | 6/2014 | Peters et al. | |
| 2014/0193468 A1 | 7/2014 | Tarrant et al. | |
| 2014/0248372 A1 | 9/2014 | Boden et al. | |
| 2014/0335147 A1 | 11/2014 | Alexakis | |
| 2015/0118277 A1* | 4/2015 | Parhami | A61P 43/00 424/423 |
| 2015/0140059 A1 | 5/2015 | Parhami et al. | |
| 2016/0159848 A1 | 6/2016 | Harrington et al. | |
| 2016/0159850 A1 | 6/2016 | Parhami et al. | |
| 2016/0317707 A1 | 11/2016 | Owens et al. | |
| 2017/0007407 A1* | 1/2017 | Reves | A61L 27/54 |
| 2017/0007739 A1 | 1/2017 | Reves et al. | |
| 2017/0022244 A1 | 1/2017 | Parhami et al. | |

FOREIGN PATENT DOCUMENTS

| | | |
|---|---|---|
| WO | 2000015274 A1 | 3/2000 |
| WO | 2005005453 A2 | 1/2005 |
| WO | 2008115469 A2 | 9/2008 |
| WO | 2009073186 A1 | 6/2009 |
| WO | 2012024581 A2 | 2/2012 |
| WO | 2012024584 A2 | 2/2012 |
| WO | 2013169399 A1 | 11/2013 |
| WO | 2014093836 A1 | 6/2014 |
| WO | 2014179756 A1 | 11/2014 |
| WO | 2015009991 A2 | 1/2015 |
| WO | 2015014872 A1 | 2/2015 |
| WO | 2015031882 A1 | 3/2015 |
| WO | 2015168636 A1 | 11/2015 |
| WO | 2016094421 A1 | 6/2016 |
| WO | 2016/205525 A1 | 12/2016 |

OTHER PUBLICATIONS

Haren, et al. Inhibition of cholesterol side-chain cleavage by intermediates of an alternative steroid biosynthetic pathway. FEBS Letters 232(2): 377-380; 1988. Retrieved on Mar. 9, 2016 from internet URL:http//onlinelibrary.wiley.com/doi/10.1016/0014-5793(88)80773-7/epdf>, entire document.

Pubchem, Compound Summary for SID 113493311, Create Date Mar. 11, 2011 retrieved from the internet Jan. 14, 2016 URL: https??pubchem.ncbi.nim.nih.gov/substance/113493311>, entire document.

International Search Report and Written Opinion of the ISA/KR dated Feb. 3, 2017 of PCT/US2016/058474 filed Oct. 24, 2016.

International Search Report and Written Opinion of the ISR/KR dated Oct. 17, 2018 of PCT/US2018/036578 filed Jun. 8, 2018.

Extended European Search Report dated Sep. 20, 2018 in European Application No. EP 18171483.3 for Oxysterol-Statin Compounds for Bone Growth, filed May 9, 2018.

Ruan, Feng, et al. Mechanisms of bone anabolism regulated by statins. Bioscience Reports, vol. 32, No. 6, Sep. 14, 2012, pp. 511-519.

Extended European Search Report dated Jul. 2, 2018 in European application EP No. 15868634.5 for Compounds and Methods Involving Sterols, filed Dec. 8, 2015.

Velgova, H., et al. On Steroids. CXXVI. Further compounds with antisclerotization effect on Pyrrhocoris apterus L. Iarvae; Structure and activity correlations. Collection Symposium Series (XIIIth Symposium on Chemistry of Nucleic Acid Components Spindleruv Mlyn, Czech Republic, Sep. 3-9, 2; [Collection Symposium Series] XX, XX, vol. 34, Jan. 1, 1969, pp. 3354-3376.

Montgomery, Scott R., et al. A Novel Osteogenic Oxysterol Compound for Therapeutic Development to Promote Bone Growth: Activation of Hedgehog Signaling and Osteogenesis Through Smoothened Binding. Journal of Bone and Mineral Research, vol. 29, No. 8, Aug. 21, 2014, pp. 1872-1885.

Burger, Alain, et al. Acetylenic cholesteryl derivatives as irreversible inhibitors of ecdysone biosynthesis. Tetrahedron, vol. 44, No. 4, Jan. 1, 1988, pp. 1141-1152.

Litvinovskaya, R. P., et al. Synthesis of 5[alpha]-hydroxyecdysteroid analogs containing an isoxazole ring in the side chain. Russian Journal of Organic Chemistry, Nauka/Interperiodica, MO, vol. 40, No. 10, Oct. 1, 2004, pp. 1456-1461.

Extended European Search Report dated Oct. 9, 2018 in European application No. EP 18174762.7 for Moldable Formulations Containing an Oxysterol in an Acellular Tissue Matrix, filed May 29, 2018.

Extended European Search Report dated Sep. 12, 2018 in European application No. EP 18168537.1 for Oxysterol-Therapeutic Agent Derivative for Bone Healing, filed Apr. 20, 2018.

Extended European Search Report dated Jul. 29, 2019 in European application No. EP 18168537.1 for Oxysterol-Therapeutic Agent Derivative for Bone Healing, filed Apr. 20, 2018.

Chinese First Office Action dated Jun. 14, 2019 in Chinese Application No. 201580076053.4 for Compounds and Methods Involving Sterols, of Warsaw Orthopedic Inc., filed Dec. 8, 2015, English translation provided.

Petrow, Vladimir, et al. 20-Hydroxycholesterol. Journal of the Chemical Soc, Chemical Society, Letchworth, GB. Jan. 1, 1956, pp. 4675-4676.

Buser, Z., et al. Effect of Oxy133, an osteogenic oxysterol, on new bone formation in rat two-level posterolateral fusion model. Eur Spine J., (2017) 26:2763-2772, May 25, 2017.

Chinese Office Action dated Jun. 29, 2021 by the Chinese State IP Office in corresponding Chinese patent application No. 201810578962.3 for Moldable Formulations Containing an Oxysterol in an Acellular Tissue Matrix.

Japanese Office Action dated Jul. 8, 2022 by the Japan Patent Office in corresponding Japanese Patent Application No. 2018-000547. English translation provided.

Japanese Office Action dated Jul. 8, 2022 by the Japan Patent Office in corresponding Japanese Patent Application No. 2018-111547. English translation provided.

* cited by examiner

MOLDABLE FORMULATIONS CONTAINING AN OXYSTEROL IN AN ACELLULAR TISSUE MATRIX

BACKGROUND

Biologics are commonly employed to promote bone growth in medical applications including fracture healing and surgical management of spinal disorders. Spine fusion is often performed by orthopedic surgeons and neurosurgeons alike to address degenerative disc disease and arthritis affecting the lumbar and cervical spine, to correct deformities caused by scoliosis, and to repair instability due to spondylolisthesis. Additionally, the techniques of spinal fusion may be applied to treat arm or leg pain caused by compressed spinal nerves. Historically, autogenous bone grafting, commonly taken from the iliac crest of the patient, has been used to augment fusion between vertebral levels.

One protein that is osteogenic and commonly used to promote spine fusion is recombinant human bone morphogenetic protein-2 (rhBMP-2). Small molecules have also been used to induce bone growth. Oxysterols form a large family of oxygenated derivatives of cholesterol that are present in the circulation, and in human and animal tissues. Oxysterols have been found to be present in atherosclerotic lesions and play a role in various physiologic processes, such as cellular differentiation, inflammation, apoptosis, and steroid production. Some naturally occurring oxysterols have robust osteogenic properties and can be used to grow bone. The most potent osteogenic naturally occurring oxysterol, 20(S)-hydroxycholesterol, is both osteogenic and anti-adipogenic when applied to multipotent mesenchymal cells capable of differentiating into osteoblasts and adipocytes.

One such oxysterol is Oxy133 or (3S,5S,6S,8R,9S,10R, 13S, 14S,17S) 17-((S)-2-hydroxyoctan-2-yl)-10, 13-dimethylhexadecahydro-1H-cyclopenta[a]phenanthrene-3,6-diol, which exhibits the following structures:

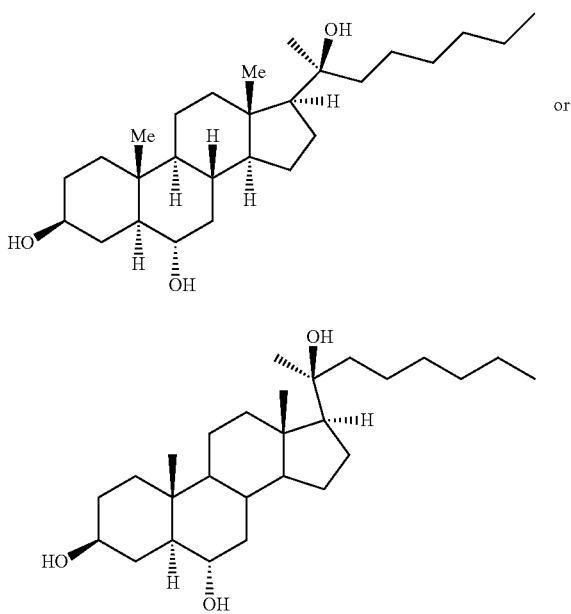

A variety of materials have been suggested for the treatment of bone defects. In addition to traditional bone grafting, a number of synthetic bone graft substitutes have been used or explored, including several matrix materials.

In recent years, much attention has been focused on the provision of materials based on collagen, either of human or animal origin. In particular, considerable attention has been directed to developing preparations and materials based on animal tissues which are treated to provide compatibility, in order to avoid rejection of the tissues when used on humans. The principal function of collagen in the dermal extracellular matrix is to act as a scaffold in connective tissue. Predominantly, collagen is present in the form of type I collagen (80-85%) and type III collagen (8-11%), both of which are fibrillar or rod-shaped collagens. The tensile strength of skin is due largely to these collagen molecules assembling into fibrils, with adjacent molecules crosslinking to further increase tensile strength. Collagen can also be used as a scaffolding material to promote bone ingrowth Collagen has frequently been used as a carrier for injectable or preformed implant compositions. The difficulty with injectable implant compositions containing collagen, elastin and/or other biocompatible material is that there is a tendency for migration and resorption and this can mean that the implant is effective only for a limited time. Pre-formed implants lend themselves to only specific procedures.

Therefore, there is a need for improved malleable implants, which can be used to deliver bone growth promoting agents. There is also a need for a collagen scaffold that collagenase cannot easily break down and can offer dimensional stability. Additionally, there is a need to provide malleable implants which can incorporate an osteogenic agent, such as an oxysterol and conveniently and quickly deliver the oxysterol to a bone defect. Furthermore, there is also a need for a malleable implant having adhesive properties to bind to other medical implants such as screws, rods, plates, and interbody devices comprising bone, allograft, autograft, and/or synthetic materials.

SUMMARY

Implants containing oxysterol uniformly disposed in an acellular tissue matrix (ATM) and methods of making and using those implants are provided. The implants are configured to fit at or near a bone defect to promote bone growth. In some embodiments, the implant is a moldable gel, paste or putty, which in some cases, can be delivered by placing it in a syringe. In other embodiments, the implant is lyophilized and, in some instances placed in a syringe for delivery to a bone defect. Upon rehydration, the implant is hydrated and, optionally, placed in a syringe for an easy delivery to a surgical site. In some embodiments, the lyophilized implants have an acellular porcine collagen matrix, which may or may not be cross-linked, bone material and an osteogenic agent, for example, an oxysterol incorporated within them. Additionally, provided are moldable implants which in addition can also include a binder or expandable phase material, for example carboxymethylcellulose, alginate, pectin or chitosan. In one aspect, the present application is directed to an implantable osteogenic medical material comprising a moldable lyophilized implant that includes a combination of an acellular porcine collagen matrix, bone material and an active agent comprising an oxysterol.

In some embodiments, provided is a moldable implant having an active agent comprising the structure:

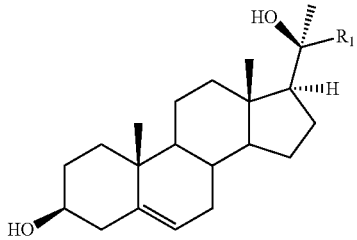

or a pharmaceutically acceptable salt, hydrate or solvate thereof, wherein $R_1$ comprises an aliphatic or cyclic substituent having at least one carbon atom. In some embodiments, the active agent is a sterol comprising Oxy133.

In certain embodiments, the acellular tissue matrix (ATM) of the implant comprises solid or semi-solid particles of collagenous material that are derived from a natural tissue material, wherein the collagenous material preserves the original fiber architecture and molecular ultrastructure of the natural tissue material from which it is derived, wherein the collagenous material is substantially free of non-fibrous tissue proteins, glycoproteins, cellular elements, lipids or lipid residues, wherein the collagenous material is non-cytotoxic, wherein the implant composition is capable of use as a component of a paste, gel or an injectable solution, and wherein the particles of collagenous material have a particle size within the range of approximately 50 microns to approximately 500 microns.

In other embodiments, the acellular tissue matrix is a non-resorbable, substantially non-antigenic collagenous fibrous tissue preparation of human or animal tissue origin, which is suitable for homo- or heterotransplantation as a permanent repair for bone defects, which preparation retains the natural structure and original architecture of the human or animal tissue, is substantially free of non-fibrous tissue proteins and glycoproteins, is substantially free of cellular elements, is substantially free of lipids and lipid residues and is non-cytotoxic, wherein the preparation is capable when implanted of being recolonized by host cells (e.g., osteoclasts, osteoblasts, etc.).

In various aspects, the acellular tissue matrix is obtained from a human, porcine, goat, bovine, ovine or equine source. In other aspects, the acellular tissue matrix is porcine collagen, which in some case, is crosslinked porcine collagen.

In some embodiments, the acellular tissue matrix of the implant comprises from about 5 wt. % to about 25 wt. % of acellular porcine collagen and from about 0.01 wt. % to about 90 wt. % oxysterol. In other embodiments, in addition to oxysterol and an acellular tissue matrix, the implant comprises a fluid from about 25 wt. % to about 50 wt. % and bone material in an amount from about 25 wt. % to about 75 wt. %.

In certain embodiments, the bone material of the implant includes demineralized bone matrix (DBM), mineralized bone matrix, demineralized bone fibers, demineralized bone chips. In other embodiments, the bone material can be inorganic ceramic comprising tricalcium phosphate, hydroxyapatite, biphasic calcium phosphate, porous calcium phosphate ceramics, tricalcium phosphate, hydroxyapatite or a combination thereof. In some aspects, tricalcium phosphate and hydroxyapatite are in a ratio of from about 70:30 to about 90:10 or in a ratio of about 85:15. In various embodiments, the particle size of the bone material is from about 125 μm to about 750 μm.

Useful fluids for the implant of this disclosure include without limitation, water, sodium chloride solution, dextrose, Lactated Ringer's solution, blood, bone marrow aspirate, bone marrow fractions, phosphate buffered saline, DMSO, acetic acid, acetone, DME, DMF, MTBE, acetonitrile, butanol, butanone, t-butyl alcohol, ethanol, polyethylene glycol, methanol, chlorobenzene, chloroform, toluene, propanol, pentane, heptane, ethanol, Capryol-90™, diethyl ether or a combination thereof. The moldable implant can also include excipients, diluents, biodegradable polymers, swelling agents, growth factors, antibiotics, solubilizers, stabilizers, bulking agents, antioxidants or binders. Useful binders or swelling agents include carboxymethylcellulose, alginate, chitosan, hydroxypropyl cellulose, hydroxypropyl methylcellulose, hydroxyethyl methylcellulose, hydroxyethylcellulose, Carbopol, propylene glycol, polyvinyl alcohols, gelatin or a combination thereof.

In some embodiments, provided is a lyophilized implant configured to fit at or near a bone defect site to promote bone growth, the implant comprising a crosslinked acellular porcine collagen in an amount of about 0.1 wt. % to about 15 wt. % of the implant and an oxysterol in an amount of about 0.01 wt. % to about 90 wt. % of the implant, the oxysterol having a concentration of from about 100 mg/cc to about 1.0 g/cc.

In some embodiments, there is a method for making an implant, the method comprising mixing a fluid with an oxysterol, the oxysterol in an amount of about 0.01 wt. % to about 90 wt. % based on the total weight of the implant and an acellular tissue matrix in an amount from about 0.1 wt. % to about 20 wt. % based on a total weight of the implant. In other embodiments, the method further comprises subjecting the implant mixed with the fluid to lyophilization to form a lyophilized implant, wherein, in some cases, the acellular tissue matrix is acellular porcine collagen or an acellular porcine crosslinked collagen.

In certain embodiments, the fluid utilized in this method is water, sodium chloride solution, dextrose, Lactated Ringer's solution, phosphate buffered saline (PBS), blood, bone marrow aspirate, bone marrow fractions or a combination thereof in an amount from about ¾ mL to about 10 mL. In other embodiments, the method further comprises adding a binder or expandable phase material in an amount from about 2 wt. % to about 4 wt. % based on a total weight of the implant. In some aspects, the binder or expandable phase material is carboxymethylcellulose, pectin, chitosan or a combination thereof.

In some embodiments, the method for making an implant further comprises placing the implant into a mold prior to lyophilization. This mold could impart features which enhance rehydration of the lyophilized implant such as recesses or holes of random or defined shapes. In other aspects, the implant can be placed into a syringe, which in some aspects, can be further placed into a vacuum sealed pouch. In other aspects, the lyophilized implant can be placed into a vacuum sealed pouch.

In some embodiments, there is a method of treating a bone defect in a patient in need thereof, the method comprising implanting at or near the bone defect an implant comprising an oxysterol uniformly dispersed in an acellular tissue matrix. In some aspects, the implant utilized in the method of treatment further comprises a binder or expandable phase material in an amount from about 2 wt. % to about 4 wt. % based on the total weight of the implant.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE FIGURES

In part, other aspects, features, benefits and advantages of the embodiments will be apparent with regard to the following description, appended claims and accompanying drawings where:

Figure 1:
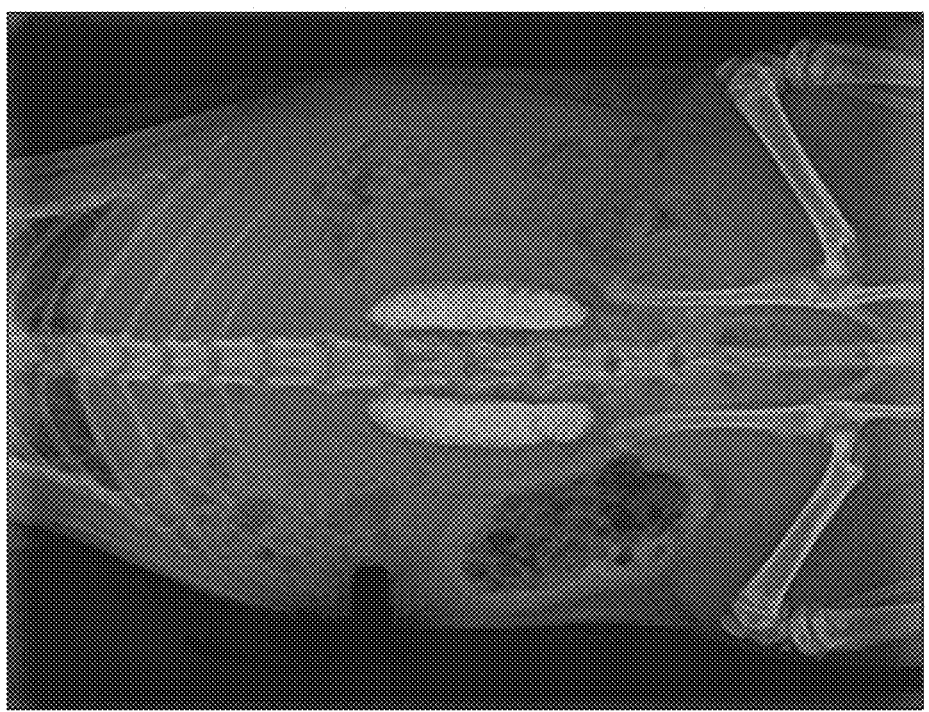
FIG. 1 illustrates an X-ray radiograph taken of a rat immediately post-operatively after undergoing a two-level posterolateral lumbar spine fusion where the implant was a malleable paste containing Permacol®, Oxy133 monohydrate, ceramic and carboxymethylcellulose.

It is to be understood that the figures may not be to scale. Further, the relationship between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present application. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the present application are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub ranges subsumed therein. For example, a range of "1 to 10" includes any and all sub ranges between (and including) the minimum value of 1 and the maximum value of 10, that is, any and all sub ranges having a minimum value of equal to or greater than 1 and a maximum value of equal to or less than 10, e.g., 5.5 to 10.

Definitions

It is noted that, as used in this specification and the appended claims, the singular forms "a," "an," and "the," include plural referents unless expressly and unequivocally limited to one referent. Thus, for example, reference to "an implant" includes one, two, three or more implants.

The term "bioactive agent" as used herein is generally meant to refer to any substance that alters the physiology of a patient. The term "bioactive agent" may be used interchangeably herein with the terms "therapeutic agent," "therapeutically effective amount," and "active pharmaceutical ingredient", "API" or "drug".

The term "biodegradable" includes compounds or components that will degrade over time by the action of enzymes, by hydrolytic action and/or by other similar mechanisms in the human body. In various embodiments, "biodegradable" includes components that can break down or degrade within the body to non-toxic components as cells (e.g., bone cells) infiltrate the components and allow repair of the defect. By "bioerodible" it is meant that the compounds or components will erode or degrade over time due, at least in part, when they come into contact with substances found in the surrounding tissue, fluids or by cellular action. By "bioabsorbable" it is meant that the compounds or components will be broken down and absorbed within the human body, for example, by a cell or tissue. "Biocompatible" means that the compounds or components will not cause substantial tissue irritation or necrosis at the target tissue site and/or will not be carcinogenic.

The term "alkyl" as used herein, refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyl such as ethanyl, ethenyl, ethynyl; propyls such as propan-1-yl, propan-2-yl, cyclopropan-1-yl, prop-1-en-1-yl, prop-1-en-2-yl, prop-2-en-1-yl, cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Where specific levels of saturation are intended, the nomenclature "alkenyl" and/or "alkynyl" is used, as defined below. In some embodiments, the alkyl groups are (C1-C40) alkyl. In some embodiments, the alkyl groups are (C1-C6) alkyl.

The term "alkanyl" as used herein refers to a saturated branched, straight-chain or cyclic alkyl radical derived by the removal of one hydrogen atom from a single carbon atom of a parent alkane. Typical alkanyl groups include, but are not limited to, methanyl; ethanyl; propanyls such as propan-1-yl, propan-2-yl(isopropyl), cyclopropan-1-yl, etc.; butyanyls such as butan-1-yl, butan-2-yl (sec-butyl), 2-methyl-propan-1-yl (isobutyl), 2-methyl-propan-2-yl (t-butyl), cyclobutan-1-yl, etc.; and the like. In some embodiments, the alkanyl groups are (C1-C40) alkanyl. In some embodiments, the alkanyl groups are (C1-C6) alkanyl.

The term "alkenyl" as used herein refers to an unsaturated branched, straight-chain or cyclic alkyl radical having at least one carbon-carbon double bond derived by the removal of one hydrogen atom from a single carbon atom of a parent alkene. The radical may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like. In some embodiments, the alkenyl group is (C2-C40) alkenyl. In some embodiments, the alkenyl group is (C2-C6) alkenyl.

The term "alkynyl" as used herein refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-3-yn-1-yl, etc.; and the like. In some embodiments, the alkynyl group is (C2-C40) alkynyl. In some embodiments, the alkynyl group is (C2-C6) alkynyl.

The term "alkyldiyl" as used herein refers to a saturated or unsaturated, branched, straight-chain or cyclic divalent hydrocarbon radical derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyls include, but are not limited to methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,3-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkanyldiyl, alkenyldiyl and/or alkynyldiyl is used. In some embodiments, the alkyldiyl group is (C1-C40) alkyldiyl. In some embodiments, the alkyldiyl group is (C1-C6) alkyldiyl. Also contemplated are saturated acyclic alkanyldiyl radicals in which the radical centers are at the terminal carbons, e.g., methandiyl (methano); ethan-1,2-diyl (ethano); propan-1,3-diyl(propano); butan-1,4-diyl(butano), and the like (also referred to as alkylenos, defined infra).

The term "alkyleno" as used herein refers to a straight-chain alkyldiyl radical having two terminal monovalent radical centers derived by the removal of one hydrogen atom from each of the two terminal carbon atoms of straight-chain parent alkane, alkene or alkyne. Typical alkyleno groups include, but are not limited to, methano; ethylenos such as ethano, etheno, ethyno; propylenos such as propano, prop[1]eno, propa[1,2]dieno, prop[1]yno, etc.; butylenos such as butano, but[1]eno, but[2]eno, buta[1,3]dieno, but[1]yno, but[2]yno, but[1,3]diyno, etc.; and the like. Where specific levels of saturation are intended, the nomenclature alkano, alkeno and/or alkyno is used. In some embodiments, the alkyleno group is (C1-C40) alkyleno. In some embodiments, the alkyleno group is (C1-C6) alkyleno.

The terms "heteroalkyl," "heteroalkanyl," "heteroalkenyl," "heteroalkynyl," "heteroalkyldiyl" and "heteroalkyleno" as used herein refer to alkyl, alkanyl, alkenyl, alkynyl, alkyldiyl and alkyleno radicals, respectively, in which one or more of the carbon atoms are each independently replaced with the same or different heteroatomic groups. Typical heteroatomic groups which can be included in these radicals include, but are not limited to, —O—, —S—, —O—O—, —S—S—, —O—S—, —NR', =N—N=, —N=N—, —N(O)N—, —N=N—NR'—, —PH—, —P(O)2-, —O—P(O)2-, —SH2-, —S(O)2-, —SnH2- or the like, where each R' is independently hydrogen, alkyl, alkanyl, alkenyl, alkynyl, aryl, arylaryl, arylalkyl, heteroaryl, heteroarylalkyl or heteroaryl-heteroaryl as defined herein.

The term "aryl" as used herein refers to a monovalent aromatic hydrocarbon radical derived by the removal of one hydrogen atom from a single carbon atom of a parent aromatic ring system. Typical aryl groups include, but are not limited to, radicals derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In some embodiments, the aryl group is (C5-C14) aryl or a (C5-C10) aryl. Some aryls are phenyl and naphthyl.

The term "aryldiyl" as used herein refers to a divalent aromatic hydrocarbon radical derived by the removal of one hydrogen atom from each of two different carbon atoms of a parent aromatic ring system or by the removal of two hydrogen atoms from a single carbon atom of a parent aromatic ring system. The two monovalent radical centers or each valency of the divalent center can form bonds with the same or different atom(s). Typical aryldiyl groups include, but are not limited to, divalent radicals derived from aceanthrylene, acenaphthylene, acephenanthrylene, anthracene, azulene, benzene, chrysene, coronene, fluoranthene, fluorine, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In some embodiments, the aryldiyl group is (C5-C14) aryldiyl or (C5-C10) aryldiyl. For example, some aryldiyl groups are divalent radicals derived from benzene and naphthalene, especially phena-1,4-diyl, naphtha-2,6-diyl and naphtha-2,7-diyl.

The term "aryleno" as used herein refers to a divalent bridge radical having two adjacent monovalent radical centers derived by the removal of one hydrogen atom from each of two adjacent carbon atoms of a parent aromatic ring system. Attaching an aryleno bridge radical, e.g. benzeno, to a parent aromatic ring system, e.g. benzene, results in a fused aromatic ring system, e.g. naphthalene. The bridge is assumed to have the maximum number of non-cumulative double bonds consistent with its attachment to the resultant fused ring system. In order to avoid double-counting carbon atoms, when an aryleno substituent is formed by taking together two adjacent substituents on a structure that includes alternative substituents, the carbon atoms of the aryleno bridge replace the bridging carbon atoms of the structure. As an example, consider the following structure:

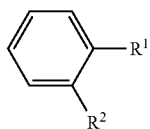

wherein $R^1$, when taken alone is hydrogen, or when taken together with $R^2$ is (C5-C14) aryleno; and $R^2$, when taken alone is hydrogen, or when taken together with $R^1$ is (C5-C14) aryleno.

When $R^1$ and $R^2$ are each hydrogen, the resultant compound is benzene. When $R^1$ taken together with $R^2$ is C6 aryleno (benzeno), the resultant compound is naphthalene. When $R^1$ taken together with $R^2$ is C10 aryleno (naphthaleno), the resultant compound is anthracene or phenanthrene. Typical aryleno groups include, but are not limited to, aceanthryleno, acenaphthyleno, acephenanthyleno, anthraceno, azuleno, benzeno (benzo), chryseno, coroneno, fluorantheno, fluoreno, hexaceno, hexapheno, hexyleno, as-indaceno, s-indaceno, indeno, naphthalene (naphtho), octaceno, octapheno, octaleno, ovaleno, penta-2,4-dieno, pentaceno, pentaleno, pentapheno, peryleno, phenaleno, phenanthreno, piceno, pleiadeno, pyreno, pyranthreno, rubiceno, triphenyleno, trinaphthaleno, or the like. Where a specific connectivity is intended, the involved bridging carbon atoms (of the aryleno bridge) are denoted in brackets, e.g., [1, 2]benzeno ([1, 2]benzo), [1, 2]naphthaleno, [2, 3]naphthaleno, etc. Thus, in the above example, when $R^1$ taken together with $R^2$ is [2, 3]naphthaleno, the resultant compound is anthracene. When $R^1$ taken together with $R^2$ is [1, 2]naphthaleno, the resultant compound is phenanthrene. In one embodiment, the aryleno group is (C5-C14) or (C5-C10).

The term "arylaryl" as used herein refers to a monovalent hydrocarbon radical derived by the removal of one hydrogen atom from a single carbon atom of a ring system in which two or more identical or non-identical parent aromatic ring systems are joined directly together by a single bond, where the number of such direct ring junctions is one less than the number of parent aromatic ring systems involved. Typical arylaryl groups include, but are not limited to, biphenyl, triphenyl, phenyl-naphthyl, binaphthyl, biphenyl-naphthyl, and the like. When the number of carbon atoms comprising an arylaryl group is specified, the numbers refer to the carbon atoms comprising each parent aromatic ring. For example, (C1-C14) arylaryl is an arylaryl group in which each aromatic ring comprises from 5 to 14 carbons, e.g., biphenyl, triphenyl, binaphthyl, phenylnaphthyl, etc. In some instances, each parent aromatic ring system of an arylaryl group is independently a (C5-C14) aromatic or a (C1-C10) aromatic. Some are arylaryl groups in which all of the parent aromatic ring systems are identical, e.g., biphenyl, triphenyl, binaphthyl, trinaphthyl, etc.

The term "biaryl" as used herein refers to an arylaryl radical having two identical parent aromatic systems joined directly together by a single bond. Typical biaryl groups include, but are not limited to, biphenyl, binaphthyl, bianthracyl, and the like. In some instances, the aromatic ring systems are (C5-C14) aromatic rings or (C5-C10) aromatic rings. In one embodiment, the biaryl group is biphenyl.

The term "arylalkyl" as used herein refers to an acyclic alkyl radical in which one of the hydrogen atoms bonded to a carbon atom, typically a terminal or spa carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylakenyl and/or arylalkynyl is used. In some embodiments, the arylalkyl group is (C6-C40) arylalkyl, e.g., the alkanyl, alkenyl or alkynyl moiety of the arylalkyl group is (C1-C26) and the aryl moiety is (C5-C14). In some embodiments, the arylalkyl group is (C6-C13), e.g., the alkanyl, alkenyl or alkynyl moiety of the arylalkyl group is (C1-C3) and the aryl moiety is (C5-C10).

The term "heteroaryl" as used herein refers to a monovalent heteroaromatic radical derived by the removal of one hydrogen atom from a single atom of a parent heteroaromatic ring system. Typical heteroaryl groups include, but are not limited to, radicals derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In some embodiments, the heteroaryl group is a 5-14 membered heteroaryl, with 5-10 membered heteroaryl. Some heteroaryl radicals are those derived from parent heteroaromatic ring systems in which any ring heteroatoms are nitrogens, such as imidazole, indole, indazole, isoindole, naphthyridine, pteridine, isoquinoline, phthalazine, purine, pyrazole, pyrazine, pyridazine, pyridine, pyrrole, quinazoline, quinoline, etc.

The term "heteroaryldiyl" refers to a divalent heteroaromatic radical derived by the removal of one hydrogen atom from each of two different atoms of a parent heteroaromatic ring system or by the removal of two hydrogen atoms from a single atom of a parent heteroaromatic ring system. The two monovalent radical centers or each valency of the single divalent center can form bonds with the same or different atom(s). Typical heteroaryldiyl groups include, but are not limited to, divalent radicals derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In some embodiments, the heteroaryldiyl group is 5-14 membered heteroaryldiyl or a 5-10 membered heteroaryldiyl. Some heteroaryldiyl groups are divalent radicals derived from parent heteroaromatic ring systems in which any ring heteroatoms are nitrogens, such as imidazole, indole, indazole, isoindole, naphthyridine, pteridine, isoquinoline, phthalazine, purine, pyrazole, pyrazine, pyridazine, pyridine, pyrrole, quinazoline, quinoline, etc.

The term "heteroaryleno" as used herein refers to a divalent bridge radical having two adjacent monovalent radical centers derived by the removal of one hydrogen atom from each of two adjacent atoms of a parent heteroaromatic ring system. Attaching a heteroaryleno bridge radical, e.g. pyridino, to a parent aromatic ring system, e.g. benzene, results in a fused heteroaromatic ring system, e.g., quinoline. The bridge is assumed to have the maximum number of non-cumulative double bonds consistent with its attachment to the resultant fused ring system. In order to avoid double-counting ring atoms, when a heteroaryleno substituent is formed by taking together two adjacent substituents on a structure that includes alternative substituents, the ring atoms of the heteroaryleno bridge replace the bridging ring atoms of the structure. As an example, consider the following structure:

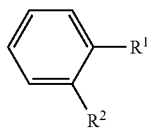

wherein $R^1$, when taken alone is hydrogen, or when taken together with $R^2$ is 5-14 membered heteroaryleno; and $R^2$, when taken alone is hydrogen, or when taken together with $R^1$ is 5-14 membered heteroaryleno;

When $R^1$ and $R^2$ are each hydrogen, the resultant compound is benzene. When R1 taken together with $R^2$ is a 6-membered heteroaryleno pyridino, the resultant compound is isoquinoline, quinoline or quinolizine. When $R^1$ taken together with $R^2$ is a 10-membered heteroaryleno (e.g., isoquinoline), the resultant compound is, e.g., acridine or phenanthridine. Typical heteroaryleno groups include, but are not limited to, acridino, carbazolo, β-carbolino, chromeno, cinnolino, furan, imidazolo, indazoleno, indoleno, indolizino, isobenzofurano, isochromeno, isoindoleno, isoquinolino, isothiazoleno, isoxazoleno, naphthyridino, oxadiazoleno, oxazoleno, perimidino, phenanthridino, phenanthrolino, phenazino, phthalazino, pteridino, purino, pyrano, pyrazino, pyrazoleno, pyridazino, pyridino, pyrimidino, pyrroleno, pyrrolizino, quinazolino, quinolino, quinolizino, quinoxalino, tetrazoleno, thiadiazoleno, thiazoleno, thiopheno, triazoleno, xantheno, or the like. Where a specific connectivity is intended, the involved bridging atoms (of the heteroaryleno bridge) are denoted in brackets, e.g., [1,2] pyridino, [2,3]pyridino, [3,4]pyridino, etc. Thus, in the above example, when $R^1$ taken together with $R^2$ is [1,2]pyridino, the resultant compound is quinolizine. When $R^1$ taken together with $R^2$ is [2,3]pyridino, the resultant compound is quinoline. When $R^1$ taken together with $R^2$ is [3,4]pyridino, the resultant compound is isoquinoline. In some embodiments, the heteroaryleno group is 5-14 membered heteroaryleno or 5-10 membered heteroaryleno. Some heteroaryleno radicals are those derived from parent heteroaromatic ring systems in which any ring heteroatoms are nitrogens, such as imidazolo, indolo, indazolo, isoindolo, naphthyridino, pteridino, isoquinolino, phthalazino, purino, pyrazolo, pyrazino, pyridazino, pyridino, pyrrolo, quinazolino, quinolino, etc.

The term "heteroaryl-heteroaryl" as used herein refers to a monovalent heteroaromatic radical derived by the removal of one hydrogen atom from a single atom of a ring system in which two or more identical or non-identical parent heteroaromatic ring systems are joined directly together by a single bond, where the number of such direct ring junctions is one less than the number of parent heteroaromatic ring systems involved. Typical heteroaryl-heteroaryl groups include, but are not limited to, bipyridyl, tripyridyl, pyridyl-purinyl, bipurinyl, etc. When the number of ring atoms are specified, the numbers refer to the number of atoms comprising each parent heteroaromatic ring systems. For example, 5-14 membered heteroaryl-heteroaryl is a heteroaryl-heteroaryl group in which each parent heteroaromatic ring system comprises from 5 to 14 atoms, e.g., bipyridyl, tripyridyl, etc. In some embodiments, each parent heteroaromatic ring system is independently a 5-14 membered heteroaromatic, in other embodiments, a 5-10 membered heteroaromatic. Also there are heteroaryl-heteroaryl groups in which all of the parent heteroaromatic ring systems are identical. Some heteroaryl-heteroaryl radicals are those in which each heteroaryl group is derived from parent heteroaromatic ring systems in which any ring heteroatoms are nitrogens, such as imidazole, indole, indazole, isoindole, naphthyridine, pteridine, isoquinoline, phthalazine, purine, pyrazole, pyrazine, pyridazine, pyridine, pyrrole, quinazoline, quinoline, etc.

The term "biheteroaryl" as used herein refers to a heteroaryl-heteroaryl radical having two identical parent heteroaromatic ring systems joined directly together by a single bond. Typical biheteroaryl groups include, but are not limited to, bipyridyl, bipurinyl, biquinolinyl, and the like. In some embodiments, the heteroaromatic ring systems are 5-14 membered heteroaromatic rings or 5-10 membered heteroaromatic rings. Some biheteroaryl radicals are those in which the heteroaryl groups are derived from a parent heteroaromatic ring system in which any ring heteroatoms are nitrogens, such as biimidazolyl, biindolyl, biindazolyl, biisoindolyl, binaphthyridinyl, bipteridinyl, biisoquinolinyl, biphthalazinyl, bipurinyl, bipyrazolyl, bipyrazinyl, bipyridazinyl, bipyridinyl, bipyrrolyl, biquinazolinyl, biquinolinyl, etc.

The term "heteroarylalkyl" as used herein refers to an acyclic alkyl radical in which one of the hydrogen atoms bonded to a carbon atom, typically a terminal or sp2 carbon atom, is replaced with a heteroaryl radical. Where specific alkyl moieties are intended, the nomenclature heteroarylalkanyl, heteroarylakenyl and/or heterorylalkynyl is used. In some embodiments, the heteroarylalkyl group is a 6-20 membered heteroarylalkyl, e.g., the alkanyl, alkenyl or alkynyl moiety of the heteroarylalkyl is 1-6 membered and the heteroaryl moiety is a 5-14-membered heteroaryl. In some embodiments, the heteroarylalkyl is a 6-13 membered heteroarylalkyl, e.g., the alkanyl, alkenyl or alkynyl moiety is 1-3 membered and the heteroaryl moiety is a 5-10 membered heteroaryl.

The term "substituted" as used herein refers to a radical in which one or more hydrogen atoms are each independently replaced with the same or different substituent(s). Typical substituents include, but are not limited to, —X, —R, —O—, =O, —OR, —O—OR, —SR, —S—, =S, —NRR, =NR, perhalo (C1-C6) alkyl, —CX3, —CF3, —CN, —OCN, —SCN, —NCO, —NCS, —NO, —NO2, =N2, —N3, —S(O)2O—, —S(O)2OH, —S(O)2R, —C(O)R, —C(O)X, —C(S)R, —C(S)X, —C(O)OR, —C(O)O—, —C(S)OR, —C(O)SR, —C(S)SR, —C(O)NRR, —C(S)NRR and —C(NR)NRR, where each X is independently a halogen (e.g., —F or —Cl) and each R is independently hydrogen, alkyl, alkanyl, alkenyl, alkanyl, aryl, arylalkyl, arylaryl, heteroaryl, heteroarylalkyl or heteroaryl-heteroaryl, as defined herein. The actual substituent substituting any particular group will depend upon the identity of the group being substituted.

The term "solvate" as used herein refers to an aggregate that comprises one or more molecules of a compound of the disclosure with one or more molecules of solvent. The solvent may be water, in which case the solvate may be a hydrate. Alternatively, the solvent may be an organic solvent. Thus, the compounds of the present disclosure may exist as a hydrate, including a monohydrate, dihydrate, hemihydrate, sesquihydrate, trihydrate, tetrahydrate or a combination thereof, as well as the corresponding solvated forms. The compound of the disclosure may be true solvates, while in other cases, the compound of the disclosure may merely retain adventitious water or be a mixture of water plus some adventitious solvent.

The term "oxysterol" as used herein is meant to encompass one or more forms of oxidized cholesterol. The oxysterols described herein are either independently or collectively active to bone growth in a patient, as described in WO 2013169399 A1, which is hereby incorporated by reference in its entirety.

The oxysterol can be in a pharmaceutically acceptable salt. Some examples of potentially pharmaceutically acceptable salts include those salt-forming acids and bases that do not substantially increase the toxicity of a compound, such as, salts of alkali metals such as magnesium, potassium and ammonium, salts of mineral acids such as hydrochloride, hydriodic, hydrobromic, phosphoric, metaphosphoric, nitric and sulfuric acids, as well as salts of organic acids such as tartaric, acetic, citric, malic, benzoic, glycollic, gluconic, gulonic, succinic, arylsulfonic, e.g., p-toluenesulfonic acids, or the like.

Pharmaceutically acceptable salts of oxysterol include salts prepared from pharmaceutically acceptable non-toxic bases or acids including inorganic or organic bases, inorganic or organic acids and fatty acids. Salts derived from inorganic bases include aluminum, ammonium, calcium, copper, ferric, ferrous, lithium, magnesium, manganic salts, manganous, potassium, sodium, zinc, and the like. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethyl amine, tripropylamine, tromethamine, and the like. When the compound of the current application is basic, salts may be prepared from pharmaceutically acceptable non-toxic acids, including inorganic and organic acids. Such acids include acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like. Fatty acid salts may also be used, e.g., fatty acid salts having greater than 2 carbons, greater than 8 carbons or greater than 16 carbons, such as butyric, caproic, caprylic, capric, lauric, mystiric, palmitic, stearic, arachidic or the like.

In some embodiments, in order to reduce the solubility of the oxysterol to assist in obtaining a controlled release depot effect, the oxysterol is utilized as the free base or utilized in a salt which has relatively lower solubility. For example, the present application can utilize an insoluble salt such as a fatty acid salt. Representative fatty acid salts include salts of oleic acid, linoleic acid, or fatty acid salts with between 8 to 20 carbons solubility, such as for example, palmeate or stearate.

The terms "bioactive" composition or "pharmaceutical" composition as used herein may be used interchangeably. Both terms refer to compositions that can be administered to a subject. Bioactive or pharmaceutical compositions are sometimes referred to herein as "pharmaceutical compositions" or "bioactive compositions" of the current disclosure. Sometimes the phrase "administration of Oxy133" is used herein in the context of administration of this compound to a subject (e.g., contacting the subject with the compound, injecting the compound, administering the compound in an implant, etc.). It is to be understood that the compound for such a use can generally be in the form of a pharmaceutical composition or bioactive composition comprising the oxysterol (e.g., Oxy133).

A "therapeutically effective amount" or "effective amount" is such that when administered, the oxysterol (e.g., Oxy133) results in alteration of the biological activity, such as, for example, enhancing bone growth, etc. The dosage administered to a patient can be as single or multiple doses depending upon a variety of factors, including the drug's administered pharmacokinetic properties, the route of administration, patient conditions and characteristics (sex, age, body weight, health, size, etc.), and extent of symptoms, concurrent treatments, frequency of treatment and the effect desired. In some embodiments the formulation is designed for immediate release. In other embodiments the formulation is designed for sustained release. In other embodiments, the formulation comprises one or more immediate release surfaces and one or more sustained release surfaces.

A "depot" includes but is not limited to capsules, microspheres, microparticles, microcapsules, microfiber particles, nanospheres, nanoparticles, coating, matrices, wafers, pills, pellets, emulsions, liposomes, micelles, gels, or other pharmaceutical delivery compositions or a combination thereof. Suitable materials for the depot are ideally pharmaceutically acceptable biodegradable and/or any bioabsorbable materials that are FDA approved or GRAS materials. These materials can be polymeric or non-polymeric, as well as synthetic or naturally occurring, or a combination thereof. In some embodiments, the matrix can be a biodegradable depot.

The term "implantable" as utilized herein refers to a biocompatible device (e.g., implant) retaining potential for successful placement within a mammal. The expression "implantable device" and expressions of the like import as utilized herein, refer to an object implantable through surgery, injection, or other suitable means whose primary function is achieved either through its physical presence or mechanical properties.

"Localized" delivery includes delivery where one or more drugs are deposited within a tissue, for example, a bone cavity, or in close proximity (within about 0.1 cm, or in many cases, within about 10 cm, for example) thereto. For example, the oxysterol dose delivered locally from the implant may be, for example, 10%, 20%, 30%, 40%, 50%, 60%, 70%, 80%, 90%, 95%, 990/%, 99.9% or 99.999% less than the oral dosage or injectable dose.

The term "mammal" refers to organisms from the taxonomy class "mammalian," including but not limited to humans, other primates such as monkeys, chimpanzees, apes, orangutans, rats, mice, rabbits, cats, dogs, pigs, cows, horses, etc.

The term "particle" refers to pieces of a substance of all shapes, sizes, thickness and configuration such as fibers, threads, narrow strips, thin sheets, clips, shards, etc., that possess regular, irregular or random geometries. It should be understood that some variation in dimension will occur in the production of the particles and particles demonstrating such variability in dimensions are within the scope of the present application. For example, the mineral particles (e.g., ceramic) can be from about 0.5 mm to about 1.5 mm. In some embodiments, the mineral particles can be from about 0.2 mm to about 0.5 mm.

In some embodiments, the medical device comprises a matrix. The "matrix" of the present application is utilized as a scaffold for bone and/or cartilage repair, regeneration, and/or augmentation. Typically, the matrix provides a 3-D matrix of interconnecting pores, which acts as a scaffold for cell migration. The morphology of the matrix guides cell migration and cells are able to migrate into or over the matrix, respectively. The cells then are able to proliferate and synthesize new tissue and form bone and/or cartilage. In some embodiments, the matrix is resorbable and comprises collagen and ceramic particles and an oxysterol uniformly distributed throughout the matrix.

In some embodiments, the matrix can be malleable, cohesive, flowable and/or can be shaped into any shape. The term "malleable" includes that the matrix is capable of being converted from a first shape to a second shape by the application of pressure.

The term "cohesive" as used herein means that the matrix tends to remain a singular, connected mass upon movement, including the exhibition of the ability to elongate substantially without breaking upon stretching. An example of a cohesive matrix includes, for example, a putty.

The term "moldable" includes that the matrix can be shaped by hand or machine or injected in the target tissue site (e.g., bone defect, fracture, or void) into a wide variety of configurations.

In some embodiments, the matrix can be formed into sheets, blocks, rings, struts, plates, disks, cones, pins, screws, tubes, teeth, bones, portion of bone, wedges, cylinders, threaded cylinders, or the like, as well as more complex geometric configurations.

The oxysterol can be "osteogenic," where it can enhance or accelerate the ingrowth of new bone tissue.

The term "acellular tissue matrix" ("ATM") refers to a tissue-derived structure that is made from any of a wide range of collagen-containing tissues by removing all, or substantially all, viable cells and, in many cases, all detectable dead cells, subcellular components and/or debris generated by dead or dying cells. As used herein, an "acellular matrix" is a matrix that: (a) is made from any of a wide range of collagen-based tissues; (b) is acellular; and (c) retains the biological and structural functions possessed by the native tissue or organ from which it was made.

The term "decellularize" refers to a process that eliminates or sufficiently reduces native cells and cellular material in a tissue such that, when such tissue is implanted, it does not invoke an adverse immune response. The term "acellular" is intended to refer to tissue that is sufficiently reduced in cells and cellular material as to not invoke an adverse immune response.

As used herein, "freeze drying" or "lyophilization," involves drying a material in a frozen state at very low pressure (e.g., in a high vacuum) so that ice, or other frozen solvent, sublimes rapidly without melting. Methods and apparatus for freeze drying are well known in the art (see, e.g., "*Freeze-Drying/Lyophilization Of Pharmaceutical and Biological Products,*" Third Edition, Louis Rey and Joan C. May, Informa Healthcare, 2010). The step of freeze drying may be carried out by any suitable method and using any suitable apparatus.

The section headings below should not be restricted and can be interchanged with other section headings.

Oxysterols

Implants containing oxysterol and methods of making and using those implants are provided. Upon rehydration, the implants can be formed to fit easily within a bone defect. In some embodiments, the implants have an acellular porcine collagen which may or may not be cross-linked, bone material and an osteogenic agent, for example, an oxysterol incorporated within them. Additionally, provided are moldable implants which in addition can also include a binder or expandable phase material, for example carboxymethylcellulose, alginate, pectin or chitosan. In one aspect, the present application is directed to an implantable osteogenic medical material comprising a moldable implant that includes a combination of an acellular porcine collagen, bone material and an active agent comprising an oxysterol.

In some embodiments, the malleable implant can be a robust implant that contains minerals or allograft material that can still bind and be cohesive. In some embodiments, there is a malleable implant configured to fit at or near a bone defect to promote bone growth, the malleable implant comprising an acellular porcine collagen in an amount of about 0.1 wt. % to about 20 wt. % of the implant, bone material in an amount of about 0.1 wt. % to about 95 wt. % of the implant, and an oxysterol, the implant configured to become moldable upon being wetted with a fluid.

Oxysterols are a family of molecules consisting of oxygenated derivatives of cholesterol. Oxysterols are involved in many biological processes, and have been found to possess osteogenic properties. For example, one naturally occurring oxysterol, 20(S)-hydroxycholesterol, has osteogenic and anti-adipogenic properties. Such oxysterols can be useful in healing bone fractures, long bone fusion procedures, spinal fusion procedures, interbody spinal fusion procedures, posterolateral spinal fusion procedures, cervical discectomy and fusion procedures, dental procedures, and cranial/maxillofacial procedures.

Oxysterols also play a role in various physiological processes, such as cellular differentiation, inflammation, apoptosis, and steroid production. Oxysterols are products of cholesterol oxidation and are formed in vivo by a variety of cell types including osteoblasts (Schroepfer. *Phyiol Rev* 80:361-554, 2000; Bjorkhem and Dicsfalusy. *Arterioscler Thromb Vase Biol* 22:734-742, 2002). Certain oxysterols, such as 20(S)-hydroxycholesterol, as well as 22(S)- or 22(R)-hydroxycholesterol, induce osteogenic differentiation in multipotent mesenchymal cells such as M2-10B4 (M2) marrow stromal cells and C3H10T1/2 embryonic fibroblasts (Kha et al. *J Bone Miner Res* 19:830-840, 2004). Oxysterols can induce osteogenesis and inhibit adipogenic differentiation of mesenchymal stem cells through activation of the hedgehog signaling pathway, which in turn regulates the master switches that control osteogenic and adipogenic differentiation, namely Runx2 and PPARγ, respectively (Richardson et al. *J Cell Biochem* 100:1131-1145, 2007; Dwyer et al. *J Biol Chem* 282: 8959-8968, 2007; Kim et al., *J Bone Miner Res* 22:1711-1719, 2007). Some oxysterols also provide therapeutic uses for treatment of bone defects or disorders such as osteoporosis.

The implants described herein can be useful in creating new therapeutic implants and matrices that include an oxysterol for induction of local bone formation and treatment of bone defects. The oxysterol is retained in the ATM and released over time, while the ATM allows influx of bone cells to grow bone and fill the defect. In some embodiments, such applications are based on the ability of these oxysterol compounds to induce the hedgehog signaling pathway. In some embodiments, the implant causes mesenchymal stem cells to show induced expression of markers of osteoblast differentiation. The implants and matrices described herein can be used for a variety of therapeutic uses including but not limited to induction of local bone formation and treatment of bone defects. In some embodiments, implants containing oxysterol as described herein induce a biological response when the implant contacts a human or animal cell. In some embodiments, the cell can be a mesenchymal stem cell or a bone marrow stromal cell. In some embodiments, the biological response comprises stimulating osteoblastic differentiation, inhibiting adipocyte differentiation, or stimulating cartilage formation. In some embodiments, the implant is configured as an implant to release the oxysterol to induce a biological response at or near a surgical site or a bone defect site.

Oxysterols can be used to induce systemic bone formation to treat bone defects such as osteoporosis, to induce local bone formation to treat conditions such as nonunion fractures, or other bone disorders, such as jaw bone defects in dental applications/implants, and to induce spinal fusion. In some embodiments, the implant may include an oxysterol alone or in combination with one or more bone morphogenetic proteins or osteogenic agents. In some embodiments, more than one oxysterol is present in the implant. In some embodiments, the implants include Oxy133 and/or Oxy153.

In some embodiments, the implant or the ATM include oxysterols which aid in osteogenesis. In some embodiments, the implant or the ATM include Oxy34, Oxy49, and/or Oxy133. In some embodiments, the implant or ATM include an oxysterol comprising the structure:

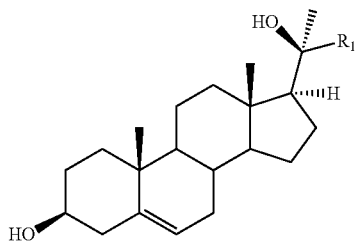

or a pharmaceutically acceptable salt, hydrate or solvate thereof, wherein $R_1$ comprises an aliphatic or cyclic substituent having at least one carbon atom.

In some embodiments, $R_1$ comprises an alkyl, a heteroalkyl, an alkanyl, a heteroalkanyl, an alkenyl, a heteroalkenyl, an alkynyl, a heteroalkynyl, an alkyldiyl, a heteroalkyldiyl, an alkyleno, a heteroalkyleno, an aryl, an aryldiyl, an arydeno, an arylaryl, a biaryl, an arylalkyl, a heteroaryl, a heteroaryldiyl, a heteroaryleno, a heteroaryl-heteroaryl, a biheteroaryl, a heteroarylalkyl or combinations thereof. In some embodiments, the $R_1$ substituent comprises a (C1-C20) alkyl or heteroalkyl, a ($C_2$-$C_{20}$) aryl or heteroaryl, a ($C_6$-$C_{26}$) arylalkyl or heteroaryl-heteroalkyl and a ($C_5$-$C_{20}$) arylalkyl or heteroaryl-heteroalkyl, a ($C_4$-$C_{10}$) alkyldiyl or heteroalkyldiyl, or a ($C_4$-$C_{10}$) alkyleno or heteroalkyleno. The $R_1$ substituent may be cyclic or acyclic, branched or unbranched, substituted or unsubstituted, aromatic, saturated or unsaturated chains, or combinations thereof. In some embodiments, the $R_1$ substituent is an aliphatic group. In some embodiments, the $R_1$ substituent is a cyclic group. In some embodiments, the $R_1$ substituent is a hexyl group.

The present disclosure includes an implant including an osteogenic oxysterol (e.g., Oxy133) uniformly disposed (e.g., dispersed) in an ATM, and the oxysterol has the ability to promote osteogenic differentiation in vitro. Oxy133 is a particularly effective osteogenic agent. In various applications, Oxy133 is useful in treating conditions that would benefit from localized stimulation of bone formation, such as, for example, spinal fusion, fracture repair, bone regenerative/tissue applications, augmentation of bone density in the jaw for dental implants, osteoporosis or the like. One particular advantage of Oxy133 is that it provides greater ease of synthesis and improved time to fusion when compared to other osteogenic oxysterols. Oxy133 is a small molecule that can serve as an anabolic therapeutic agent for bone growth, as well as a useful agent for treatment of a variety of other conditions.

Compositions and methods for preparing Oxy133 have been described in International Application No. PCT/2015/064526 filed on Dec. 8, 2015, the contents of which is incorporated herein by reference in its entirety.

One aspect of the application disclosure is an implant or a ATM including Oxy133, having the formula:

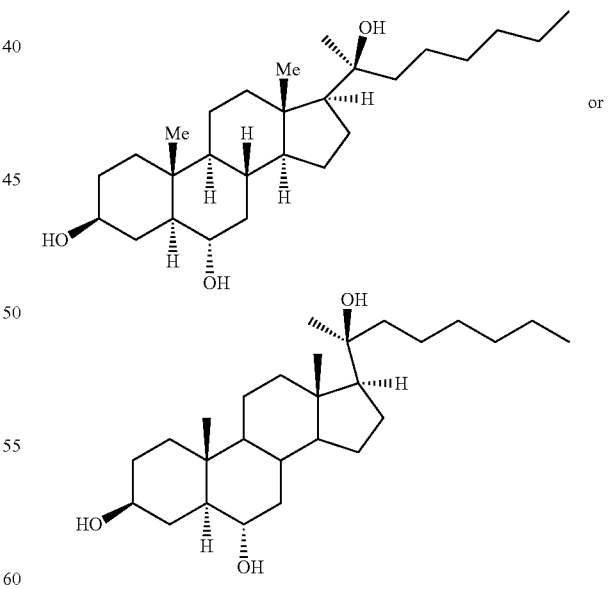

or a pharmaceutically acceptable salt, solvate or hydrate thereof. The Oxy133 may be used as a bioactive or pharmaceutical composition comprising Oxy133 or a pharmaceutically acceptable salt, solvate or hydrate thereof and a pharmaceutically acceptable carrier. Oxy133 has the IUPAC designation (3S,5S,6S,8R,9S, 1 OR, 13S, 14S, 17S)-17-((S)-

2-hydroxyoctan-2-yl)-10,13-dimethylhexadecahydro-1H-cyclopenta[a]phenanthrene-3,6-diol.

Another aspect of the disclosure is a method for inducing (stimulating, enhancing) a hedgehog (Hh) pathway mediated response, in a cell or tissue, comprising contacting the cell or tissue with a therapeutically effective amount of Oxy133. The cell or tissue can be in vitro or in a subject, such as a mammal. The hedgehog (Hh) pathway mediated response involves the stimulation of osteoblastic differentiation, osteomorphogenesis, and/or osteoproliferation; the stimulation of hair growth and/or cartilage formation; the stimulation of neovasculogenesis, e.g., angiogenesis, thereby enhancing blood supply to ischemic tissues; or it is the inhibition of adipocyte differentiation, adipocyte morphogenesis, and/or adipocyte proliferation; or the stimulation of progenitor cells to undergo neurogenesis. The Hh mediated response can comprise the regeneration of any of a variety of types of tissues, for use in regenerative medicine. Another aspect of the disclosure is a method for treating a subject having a bone disorder, osteopenia, osteoporosis, or a bone fracture, comprising administering to the subject an effective amount of a bioactive composition or pharmaceutical composition comprising Oxy133. The subject can be administered the bioactive composition or pharmaceutical composition at a therapeutically effective dose, in an effective dosage form at a selected interval to, e.g., increase bone mass, ameliorate symptoms of osteoporosis, reduce, eliminate, prevent or treat atherosclerotic lesions, or the like. The subject can be administered the bioactive composition or pharmaceutical composition at a therapeutically effective dose, in an effective dosage form at a selected interval to ameliorate the symptoms of osteoporosis. In some embodiments, a composition comprising Oxy133 may include mesenchymal stem cells to induce osteoblastic differentiation of the cells at a targeted surgical area.

In various aspects, the Oxy133 can be administered to a cell, tissue or organ by local administration. For example, the Oxy133 can be applied locally with a cream or the like, or it can be injected or otherwise introduced directly into a cell, tissue or organ, or it can be introduced with a suitable medical device, such as an implant as discussed herein.

In some embodiments, the dosage of Oxy133 is from approximately 10 pg/day to approximately 80 g/day. In some embodiments, the dosage of Oxy133 is from about 1.0 g/day, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5, 40.0, 40.5, 41.0, 41.5, 42.0, 42.5, 43.0, 43.5, 44.0, 44.5, 45.0, 45.5, 46.0, 46.5, 47.0, 47.5, 48.0, 48.5, 49.0, 49.5 50.0, 50.5, 51.0, 51.5, 52.0, 52.5, 53.0, 53.5, 54.0, 54.5, 55.0, 55.5, 56.0, 56.5, 57.0, 57.5, 58.0, 58.5, 59.0, 59.5 to about 60.0 grams/day. Additional dosages of Oxy133 include from approximately 2.4 ng/day to approximately 50 mg/day; approximately 50 ng/day to approximately 2.5 mg/day; approximately 250 ng/day to approximately 250 mcg/day; approximately 250 ng/day to approximately 50 mcg/day; approximately 250 ng/day to approximately 25 mcg/day; approximately 250 ng/day to approximately 1 mcg/day; approximately 300 ng/day to approximately 750 ng/day or approximately 0.50 mcg/day to 500 ng/day. In various embodiments, the dose may be about 0.01 to approximately 10 mcg/day or approximately 1 ng/day to about 120 mcg/day. In some embodiments, the dosage of Oxy133 is in greater amounts. For example, in some embodiments, the dosage of Oxy133 is from 0.01 mg/day to 5 g/day.

An acellular tissue matrix (ATM) can comprise the oxysterol (e.g., Oxy133) disposed homogenously throughout it or in discrete regions or discrete layers of the ATM. The oxysterol can be loaded in the ATM and can comprise from about 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5, 40.0, 40.5, 41.0, 41.5, 42.0, 42.5, 43.0, 43.5, 44.0, 44.5, 45.0, 45.5, 46.0, 46.5, 47.0, 47.5, 48.0, 48.5, 49.0, 49.5, 50.0, 50.5, 51.0, 51.5, 52.0, 52.5, 53.0, 53.5, 54.0, 54.5, 55.0, 55.5, 56.0, 56.5, 57.0, 57.5, 58.0, 58.5, 59.0, 59.5 to about 600/% w/v, w/w and/or v/v of the total weight of the ATM.

In some embodiments, a high concentration of the oxysterol can be loaded into the ATM and comprises from about 20 wt. % to about 99 wt. % of the ATM. In some embodiments, the oxysterol can be loaded into the ATM in an amount from about 20 wt. % to about 90 wt. %, 35 wt. % to about 80 wt. % or about 50 wt. % to about 90 wt. % of the ATM. In some embodiments, the oxysterol can be loaded into the ATM in an amount of about 20 wt. % to about 30 wt. %, about 30 wt. % to about 40 wt. %, about 40 wt. % to about 50 wt. %, about 50 wt. % to about 60 wt. %, about 60 wt. % to about 70 wt. %, about 70 wt. % to about 80 wt. %, about 80 wt. % to about 90 wt. %, or about 90 wt. % to about 99 wt. %. In some embodiments, the oxysterol can be loaded into the ATM in an amount of from about 20, 25, 30, 35, 40, 45, 50, 55, 60, 65, 70, 75, 80, 85, 90, 95, to about 99 wt. % of the ATM.

The oxysterol can be loaded in the ATM and can comprise from about 0.01, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5, 40.0, 40.5, 41.0, 41.5, 42.0, 42.5, 43.0, 43.5, 44.0, 44.5, 45.0, 45.5, 46.0, 46.5, 47.0, 47.5, 48.0, 48.5, 49.0, 49.5, 50.0, 50.5, 51.0, 51.5, 52.0, 52.5, 53.0, 53.5, 54.0, 54.5, 55.0, 55.5, 56.0, 56.5, 57.0, 57.5, 58.0, 58.5, 59.0, 59.5 to about 60 mg/cc of the ATM. In some embodiments, the oxysterol can be loaded into the ATM in an amount of about 400 mg/cc. In some embodiments, the oxysterol can be loaded into the ATM in an amount of from about 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, to about 500 mg/cc. In some embodiments, 400 mg/cc can be loaded in the ATM.

In some embodiments, the oxysterol can be loaded into the ATM in highly concentrated amounts. For example, in some embodiments, the oxysterol is loaded into the ATM in an amount of at least 500 mg/cc. In some embodiments, the oxysterol is added into the ATM in an amount of about 1 mg/cc to about 1 g/cc, from about 100 mg/cc to about 1 g/cc, from about 500 mg/cc to about 900 mg/cc, or from about 600 mg/cc to about 800 mg/cc. In other embodiments, the oxysterol is added into the ATM in an amount of from about 500 mg/cc to about 600 mg/cc, from about 600 mg/cc to about 700 mg/cc, from about 700 mg/cc to about 800 mg/cc, from about 800 mg/cc to about 900 mg/cc, or from about 900 mg/cc to about 1 g/cc.

In addition to the compound Oxy133, other embodiments of the disclosure encompass any and all individual stereoisomers at any of the stereocenters present in Oxy133, including diastereomers, racemates, enantiomers, and other isomers of the compound. In embodiments of the disclosure, Oxy133 may include all polymorphs, solvates or hydrates of the compound, such as hydrates and those formed with organic solvents. In various embodiments, Oxy133 includes polymorph Form A, polymorph Form B, polymorph Form C, polymorph Form D, polymorph Form E, polymorph Form F, polymorph Form G, polymorph Form H, polymorph Form I or a mixture thereof as described in U.S. Ser. Nos. 15/082,695 and 15/374,610 incorporated herein by reference as if set forth in full.

In some embodiments, the oxysterol that can be distributed uniformly in the acellular tissue matrix can be an Oxy133 polymorph which comprises, consists essentially of, or consists of polymorph Form A, and/or polymorph Form B. In some embodiments, the Oxy133 polymorph comprises, consists essentially of, or consists of Form A that produces an X-ray powder diffraction pattern comprising one or more of the following reflections: 16.4, 17.91 and 20.94±0.2 degree 2θ. In some embodiments, the Oxy133 polymorph comprises, consists essentially of, or consists of Form A that produces an X-ray powder diffraction pattern comprising one or more of the following reflections: 6.1, 12.3, and 18.6±0.2 degree 2θ in place of or in addition to the X-ray powder diffraction pattern of those above for Form A.

In some embodiments, polymorph Oxy133 that can be distributed uniformly in the acellular tissue matrix comprises, consists essentially of, or consists of Form B that produces an X-ray powder diffraction pattern comprising one or more of the following reflections: 13.3, 16.1, and 18.82±0.2 degree 2θ. In some embodiments, the Oxy133 polymorph comprises, consists essentially of, or consists of Form B that produces an X-ray powder diffraction pattern comprising one or more of the following reflections: 5.9, 11.9, and 17.96±0.2 degree 2θ in place of or in addition to the X-ray powder diffraction pattern of those above for Form B.

The ability to prepare salts depends on the acidity or basicity of a compound. Suitable salts of the compound include, but are not limited to, acid addition salts, such as those made with hydrochloric, hydrobromic, hydroiodic, perchloric, sulfuric, nitric, phosphoric, acetic, propionic, glycolic, lactic, pyruvic, malonic, succinic, maleic, fumaric, malic, tartaric, citric, benzoic, carbonic, cinnamic, mandelic, methanesulfonic, ethanesulfonic, hydroxyethanesulfonic, benezenesulfonic, p-toluene sulfonic, cyclohexanesulfamic, salicyclic, p-aminosalicylic, 2-phenoxybenzoic, and 2-acetoxybenzoic acid; salts made with saccharin; alkali metal salts, such as sodium and potassium salts; alkaline earth metal salts, such as calcium and magnesium salts; and salts formed with organic or inorganic ligands, such as quaternary ammonium salts. Additional suitable salts include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylgucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate salts of the compounds.

In various embodiments, Oxy133 includes one or more biological functions. That is, Oxy133 can induce a biological response when contacted with a mesenchymal stem cell or a bone marrow stromal cell. For example, Oxy133 may stimulate osteoblastic differentiation. In some embodiments, a bioactive composition including Oxy133 may include one or more biological functions when administered to a mammalian cell, for example, a cell in vitro or a cell in a human or an animal. For example, such a bioactive composition may stimulate osteoblastic differentiation. In some embodiments, such a biological function can arise from stimulation of the hedgehog pathway.

Purification of Oxy133

In some embodiments, the oxysterol, for example Oxy133, is highly purified. In some embodiments, the Oxy133 may be crystallized or recrystallized. In some embodiments, purified Oxy133 is formed by recrystallizing Oxy133 in a 3:1 mixture of acetone/water, as shown below:

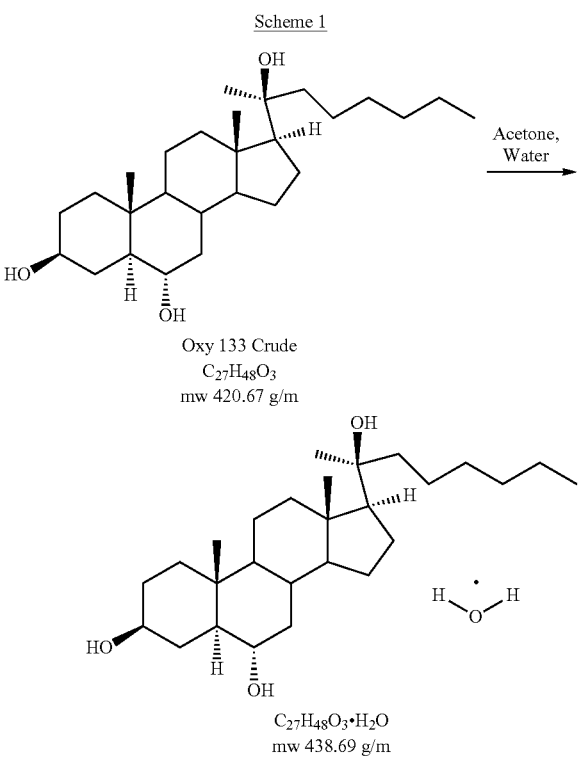

As shown above, upon crystallization, the purified Oxy133 forms a hydrate. However, in some embodiments, the Oxy133 is in the anhydrous form. In some embodiments, the percent crystallinity of any of the crystalline forms of Oxy133 described herein can vary with respect to the total amount of Oxy133.

In certain embodiments, the Oxy133 can have a percent crystallinity of a salt, hydrate, solvate or crystalline form of Oxy133 to be from about at least 10%, at least 20%, at least 30%, at least 40%, at least 50%, at least, 60%, at least 70%, at least 80%, at least 90%, at least 95%, or to at least 99%. In some embodiments, the percent crystallinity can be substantially 100%, where substantially 100% indicates that the entire amount of Oxy133 appears to be crystalline as best as can be determined using methods known in the art. Accordingly, therapeutically effective amounts of Oxy133 can include amounts that vary in crystallinity. These include instances where an amount of the crystallized Oxy133 in a solid form is subsequently dissolved, partially dissolved, or suspended or dispersed in a liquid.

In one embodiment, the purified Oxy133 is crystallized as a monohydrate. However, in other embodiments the purified Oxy133 may be crystallized in other hydrous forms, such as, for example, a dihydrate, a hemihydrate, a sesquihydrate, a trihydrate, a tetrahydrate or combinations thereof, as well as the corresponding solvated forms. In some embodiments, the Oxy133 is crystallized in an amorphous form. In other embodiments, the purified Oxy133 is crystallized as a co-crystal or a pharmaceutically acceptable salt.

In some embodiments, the oxysterol (e.g., Oxy133) that can be used can be in amorphous form and have faster dissolution and release from the ATM, such as, for example, a burst release from the ATM of from about 10%, 15%, 20%, 25%, 30%, 35%, 45%, to about 50% of the oxysterol over 24 or 48 hours.

In some embodiments, the unpurified Oxy133 may be solidified by mixing with heptanes. The product may be subsequently filtered and suspended in methylene chloride. In some embodiments, the unpurified Oxy133 may be filtered from the suspension and crystallized with the use of acetone and water or other organic or inorganic solvents (e.g., diethyl ether, dichloromethane, ethyl acetate, acetone, n,n-dimethylformamide, acetonitrile, dimethyl sulfoxide, ammonia, t-butanol, n-propanol, ethanol, methanol, acetic acid or a combination thereof).

In various embodiments, the unpurified Oxy133 may be isolated and purified by any other traditional means. That is, the unpurified Oxy133 can be isolated and purified to the desired purity, e.g., from about 95% to about 99.9% by filtration, centrifugation, distillation to separate volatile liquids on the basis of their relative volatilities, crystallization, recrystallization, evaporation to remove volatile liquids from non-volatile solutes, solvent extraction to remove impurities, dissolving the composition in a solvent in which other components are soluble therein or other purification methods.

In some embodiments, the purified Oxy133 is formed in crystal form via crystallization, which separates the Oxy133 from the liquid feed stream by cooling the liquid feed stream or adding precipitants which lower the solubility of byproducts and unused reactants in the reaction mixture so that the Oxy133 forms crystals. In some embodiments, the solid crystals are then separated from the remaining liquid by filtration or centrifugation. The crystals can be resolubilized in a solvent and then recrystallized and the crystals are then separated from the remaining liquid by filtration or centrifugation to obtain a highly pure sample of Oxy133. In some embodiments, the crystals can then be granulated to the desired particle size. In some embodiments, mineral particles (e.g., ceramic) can be used in the ATM and can have a particle size of from about 0.5 mm to about 1.5 mm. In some embodiments, the mineral particles can be from about 0.2 mm to about 0.5 mm.

In some embodiments, the unpurified Oxy133 can be purified where the purified Oxy133 is formed in crystalized form in a solvent and then removed from the solvent to form a high purity Oxy133 having a purity of from about 98% to about 99.99%. In some embodiments, the Oxy133 can be recovered via filtration or vacuum filtration before or after purification.

Implants

In some embodiments, the implant comprises an ATM that provides an acellular tissue scaffold for cells to guide the process of tissue formation in vivo in three dimensions in addition to the oxysterol (e.g., Oxy133). In some embodiments, the implant provides a porous scaffold to promote bone ingrowth. The morphology of the ATM guides cell migration and cells are able to migrate into or over the ATM. The cells then are able to proliferate and synthesize new tissue and form bone and/or cartilage. In some embodiments, one or more acellular tissue matrices are stacked on one another.

In some embodiments, the implant comprises an oxysterol uniformly disposed in a cohesive mass of an ATM. In certain embodiments, the ATM is obtained from a human, porcine, goat, bovine, ovine or equine source. In other aspects, the ATM is porcine collagen, while in other aspects, the ATM is crosslinked porcine collagen. In various aspects, the implant is a moldable gel, paste or putty and may be placed in a syringe. In certain aspects, the implant can be lyophilized and hydrated and then placed at a bone defect site by a surgeon or other responsible professional. In other aspects the lyophilized implant is hydrated and placed in a syringe for delivery to a bone defect site.

In some embodiments, the implant comprises bone material in addition to the ATM and the oxysterol. The ATM may be obtained from a human or animal source, and in some cases, may be non-crosslinked, while in other cases the ATM may be crosslinked. In various cases, the ATM comprises acellular porcine collagen, which, in some cases, can be crosslinked. Each of the acellular porcine collagen, bone material and oxysterol comprise particles which are homogenously mixed with each other. In various embodiments, the bone material comprises demineralized bone (DBM) ATM, mineralized bone ATM, demineralized bone fibers, demineralized bone chips; and inorganic ceramic comprising tricalcium phosphate, hydroxyapatite, biphasic calcium phosphate, porous calcium phosphate ceramics, or tricalcium phosphate, hydroxyapatite or a combination thereof. In some embodiments, the implant also comprises a binder or expandable phase or swelling agent, for example, carboxymethylcellulose or other cellulose derivatives.

The moldable implant, in some embodiments, comprises a porous body that includes a particulate mineral material having an average particle diameter of from about 0.4 mm to about 5.0 mm homogenously mixed with an ATM. In some embodiments, the mineral particles have an average particle size of from about 0.5 mm to about 1.5 mm. In some embodiments, the mineral particles have an average particle size of from about 125 micrometers to about 750 micrometers.

In some embodiments, the particulate minerals (e.g., TCP: HA) can be homogenously disposed throughout the ATM at a particle size of from about 0.10, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39, 0.40, 0.41, 0.42, 0.43, 0.44, 0.45, 0.46, 0.47, 0.48, 0.49, 0.50, 0.51, 0.52, 0.53, 0.54, 0.55, 0.56, 0.57, 0.58, 0.59, 0.60, 0.61, 0.62, 0.63, 0.64, 0.65, 0.66, 0.67, 0.68, 0.69, 0.70, 071, 0.72, 0.73, 0.74, 0.75, 0.76, 0.77, 0.78, 0.79, 0.80, 0.81, 0.82, 0.83, 0.84, 0.85, 0.86, 0.87, 0.88, 0.89, 0.90, 0.91, 0.92, 0.93, 0.94, 0.95, 0.96, 0.97, 0.98, 0.99, 1.0, 1.25, 1.4, 1.5, 1.6, 1.7, 1.8, 1.9, 2.0, 2.25 to about 2.5 mm. These particles can be in the form of granules, chips, fibers or a combination thereof.

In various embodiments, the particle size distribution of the ATM may be from about 10 micrometers, 13 micrometers, 85 micrometers, 100 micrometers, 151 micrometers, 200 micrometers and all subranges therebetween. In some embodiments, at least 75% of the particles have a size from about 10 micrometers to about 200 micrometers. In some embodiments, at least 85% of the particles have a size from about 10 micrometers to about 200 micrometers. In some embodiments, at least 95% of the particles have a size from about 10 micrometers to about 200 micrometers. In some embodiments, all of the particles have a size from about 10 micrometers to about 200 micrometers. In some embodiments, at least 75% of the particles have a size from about 20 micrometers to about 180 micrometers. In some embodiments, at least 85% of the particles have a size from about 20 micrometers to about 180 micrometers. In some embodiments, at least 95% of the particles have a size from about 20 micrometers to about 180 micrometers. In some embodiments, all of the particles have a size from about 20 micrometers to about 180 micrometers.

In some embodiments, the one or more oxysterols may for example have an average particle size of from about 2.2 to about 10 microns. In some embodiments the oxysterol particles have a minimum average particle size of about 2.2 microns, or about 2.5 microns, or about 3 microns, or about 4 microns. The particles also may have a maximum average particle size of about 10 microns, or about 8 microns, or about 7 microns, or about 5 microns. In some embodiments, the oxysterol has a particle size from about 5 to 30 micrometers, or about 2 microns to about 20 microns, or from 30 microns to 100 microns, however, in various embodiments, ranges from about 1 micron to 250 microns may be used. In some embodiments, the oxysterol has a particle size of about 0.1 nm to about 1 micron to provide enhanced dissolution and quicker release from the implant. In some embodiments, the oxysterol (e.g., Oxy133) is in nanoparticle form and from about 10.0, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, to about 500 nm in diameter.

In some embodiments, the oxysterol includes a particle size of about 0.1 mm to about 5 mm to lengthen the release duration from the implant by slowing down Oxy133 dissolution rate which might modulate bone formation. Moreover, the oxysterol particles may have a monophasic distribution. Additionally, in some embodiments, it may be useful to have a water-soluble oxysterol in order to produce an acute anti-inflammatory/analgesic effect that the implant is not providing.

In various embodiments, the oxysterol is in the form of a polymorph, solvate, hydrate or a pharmaceutically acceptable salt. The oxysterol may alternatively be crystallized in an amorphous form. In some embodiments, the oxysterol is in the form of a monohydrate. In some embodiments, the oxysterol (e.g., Oxy133) may be in amorphous form. In various embodiments, the implant comprises Oxy133 and an ATM in amorphous, crystalline or semi-crystalline form; where the crystalline form may include polymorphs, solvates or hydrates. Oxy133 includes polymorph Form A, polymorph Form B, polymorph Form C, polymorph Form D, polymorph Form E, polymorph Form F, polymorph Form G, polymorph Form H, polymorph Form I or a mixture thereof as described in U.S. Ser. Nos. 15/082,695 and 15/374,610 incorporated herein by reference as if set forth in full.

In some embodiments, an ATM of the present application includes an oxysterol in an amount from about 0.01 mg/cc to about 500 mg/cc. The ATM may include the oxysterol in an amount of from about 10 mg/cc, 20 mg/cc, 25 mg/cc, 30 mg/cc, 40 mg/cc, 50 mg/cc, 60 mg/cc, 70 mg/cc, 80 mg/cc, 90 mg/cc, 100 mg/cc, 110 mg/cc, 120 mg/cc, 130 mg/cc, 140 mg/cc, 150 mg/cc, 160 mg/cc, 170 mg/cc, 180 mg/cc, 190 mg/cc, 200 mg/cc, 210 mg/cc, 220 mg/cc, 230 mg/cc, 240 mg/cc, 250 mg/cc, 260 mg/cc, 270 mg/cc, 280 mg/cc, 290 mg/cc, 300 mg/cc, 310 mg/cc, 320 mg/cc, 330 mg/cc, 340 mg/cc, 350 mg/cc, 360 mg/cc, 370 mg/cc, 380 mg/cc, 390 mg/cc, 400 mg/cc, 410 mg/cc, 420 mg/cc, 430 mg/cc, 440 mg/cc, 450 mg/cc, 460 mg/cc, 470 mg/cc, 480 mg/cc, 490 mg/cc, to about 500 mg/cc or any amount therebetween. In some embodiments, the ATM releases from about 40 ng to about 5 mg of the oxysterol every hour.

In some embodiments, the oxysterol can be loaded into the ATM in highly concentrated amounts. For example, in some embodiments, the oxysterol is loaded into the ATM in an amount of at least 500 mg/cc. In some embodiments, the oxysterol is added to the ATM in an amount of about 1 mg/cc to about 1 g/cc, from about 100 mg/cc to about 1 g/cc, from about 500 mg/cc to about 900 mg/cc, or from about 600 mg/cc to about 800 mg/cc. In other embodiments, the oxysterol is added to the ATM in an amount of about 500 mg/cc to about 600 mg/cc, about 600 mg/cc to about 700 mg/cc, about 700 mg/cc to about 800 mg/cc, about 800 mg/cc to about 900 mg/cc, or about 900 mg/cc to about 1 g/cc. In some embodiments, the oxysterol is loaded into the ATM in an amount of about 134 mg/cc.

In some embodiments, the oxysterol comprises a range of about 0.01 wt. % to about 45 wt. % based on the total weight of the ATM or the implant prior to or after being wetted. In some embodiments, the implant comprises at least one biodegradable material in a wt. % of from about 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, or to about 44% based on the total weight of the ATM or the implant.

In some embodiments, the ATM containing the oxysterol may have a burst release surface that releases from about 10%, 15%, 20%, 25%, 30%, 35%, 45%, to about 50% of the oxysterol over 24 or 48 hours.

In some embodiments, a high concentration of the oxysterol can be loaded into the ATM and comprise from about 0.01 wt. % to about 90 wt. % of the ATM. In some embodiments, the oxysterol can be loaded into the ATM in an amount from about 0.1 wt. % to about 90 wt. % or from about 1.0 wt. % to about 90 wt. % of the ATM. In some embodiments, the oxysterol can be loaded into the ATM in an amount of from about 20 wt. % to about 30 wt. %, about 30 wt. % to about 40 wt. %, about 40 wt. % to about 50 wt. %, about 50 wt. % to about 60 wt. %, about 60 wt. % to about 70 wt. %, about 70 wt. % to about 80 wt. %, about 80 wt. % to about 90 wt. %, or about 90 wt. % to about 99 wt. % of the ATM. In some embodiments, the oxysterol can be loaded into the ATM in an amount of from about 20, 25, 30, 35, 40, 45, 50, 55, 60, 65, 70, 75, 80, 85, 90, or to about 95 wt. % of the ATM.

In some embodiments, the ATM releases the oxysterol over a period of 1-90 days, 1-10 days, 1-3 days, 3-7 days, 3-12 days, 3-14 days, 7-10 days, 7-14 days, 7-21 days, 7-30 days, 7-50 days, 7-90 days, 7-140 days, 14-140 days, 3 days to 135 days, 3 days to 180 days, or 3 days to 6 months. In some embodiments, bone growth will be observed over a period of at least 14 days, for example, 14-90 days, 14-30 days, 14-60 days, 21-90 days, 21-180 days; 14-210 days, or 14 days to 6 months.

In some embodiments, the ATM (in some cases, acellular porcine collagen) comprises from about 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5, 40.0, 40.5, 41.0, 41.5, 42.0, 42.5, 43.0, 43.5, 44.0, 44.5, 45.0, 45.5, 46.0, 46.5, 47.0, 47.5, 48.0, 48.5, 49.0, 49.5, or to about 50.0% w/w, w/v or v/v of the implant. In certain embodiments, the ATM is acellular porcine collagen, which can be present in an amount of about 0.1 wt. % to about 25 wt. % of the implant. In some embodiments, the ATM is present in an amount between about 0.01 wt. % to about 50 wt. %, about 0.1 wt. % to about 20 wt. % or about 0.1 wt. % to about 25 wt. % of the implant. In some embodiments, the ATM is acellular crosslinked porcine collagen, which can be present in an amount of from about 0.1 wt. % to about 25 wt. %, about 1.0 wt. % to about 20 wt. %, about 20 wt. % to about 30 wt. %, about 30 wt. % to about 40 wt. %, or about 40 wt. % to about 50 wt. %.

In some embodiments, the implant further comprises a fluid from about 25 wt. % to about 50 wt. % which is added to enhance the malleability of the moldable implant. The malleable implant is configured to be moldable to any desired shape to fit a bone defect site. In some embodiments, the malleable implant may be molded to fit into a surgical site, such as a bone defect site. The shape of the ATM may be tailored to the site at which it is to be situated. For example, it may be in the shape of a morsel, a plug, a pin, a peg, a cylinder, a block, a wedge, a sheet, a strip, etc. The term "shape" refers to a determined or regular form or configuration in contrast to an indeterminate or vague form or configuration (as in the case of a lump or other solid mass of no special form) and is characteristic of such materials as sheets, strips, plates, disks, cores, tubes, wedges, cylinders, or the like. This includes forms ranging from regular, geometric shapes to irregular, angled, or non-geometric shapes, or combinations of features having any of these characteristics. In some embodiments, the implant is malleable prior to being implanted into a surgical site. In such embodiments, a medical practitioner may mold the implant to a desired shape and allow the implant to cure or dry prior to implantation. In such embodiments, a medical practitioner may mold the implant directly into a bone defect site. The implant is malleable and configured to be pressed into a bone defect site to fill out crevices in a bone defect site. In some embodiments, the implant is malleable when wetted and is configured to remain malleable while in contact with a bone defect site. In certain embodiments, the moldable implant is placed in a syringe for delivery to a bone defect site. The syringe containing the implant can also be placed into a vacuum sealed pouch.

In some embodiments, the malleable ATM can be formed to fit into the void space of an interbody cage or around the outside of the cage in the intervertebral space.

The implant may be wetted or hydrated with a variety of fluids to form a malleable and moldable implant or a slurry that can be subsequently lyophilized. In some embodiments, the ATM is wetted with sterile water, physiological saline, sodium chloride, dextrose, Lactated Ringer's solution, phosphate buffered saline (PBS), blood, bone marrow aspirate, bone marrow fractions or a combination thereof. The amount of fluid that the ATM can be wetted with includes from about 0.25, 0.5, 0.75, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 20.5, 21.0, 21.5, 22.0, 22.5, 23.0, 23.5, 24.0, 24.5, 25.0, 25.5, 26.0, 26.5, 27.0, 27.5, 28.0, 28.5, 29.0, 29.5, 30.0, 30.5, 31.0, 31.5, 32.0, 32.5, 33.0, 33.5, 34.0, 34.5, 35.0, 35.5, 36.0, 36.5, 37.0, 37.5, 38.0, 38.5, 39.0, 39.5, 40.0, 40.5, 41.0, 41.5, 42.0, 42.5, 43.0, 43.5, 44.0, 44.5, 45.0, 45.5, 46.0, 46.5, 47.0, 47.5, 48.0, 48.5, 49.0, 49.5 to about 50.0 mL.

In some embodiments, the implant is hydrated with hyaluronic acid, cellulose ethers (such as carboxymethylcellulose), collagen, gelatin, autoclaved bone powder, osteoconductive carriers, whole blood, blood fractions, bone marrow aspirate, concentrated bone marrow aspirate, and mixtures thereof. Non-limiting examples of blood fractions include serum, plasma, platelet-rich plasma (PRP), concentrated platelet-rich plasma, platelet-poor plasma, and concentrated platelet poor plasma. After hydrating, the implant becomes a gel, a putty or a paste that can be molded into a predetermined shape in about 30 seconds or administered to a bone defect and manipulated to conform to the bone defect in such a manner that will promote healing.

In some embodiments, the implant comprises a porous ATM configured to allow influx of at least bone and/or cartilage cells therein. In some embodiments, the ATM is also configured to release an active agent, such as an oxysterol. By "porous," it is meant that the ATM has a plurality of pores. The pores of the ATM are a size large enough to allow influx of blood, other bodily fluid, and progenitor and/or bone and/or cartilage cells into the interior to guide the process of tissue formation in vivo in three dimensions.

In some embodiments, the ATM comprises a plurality of pores. In some embodiments, at least 10% of the pores are between about 50 micrometers and about 500 micrometers at their widest points. In some embodiments, at least 20% of the pores are between about 50 micrometers and about 250 micrometers at their widest points. In some embodiments, at least 30% of the pores are between about 50 micrometers and about 150 micrometers at their widest points. In some embodiments, at least 50% of the pores are between about 10 micrometers and about 500 micrometers at their widest points. In some embodiments, at least 90% of the pores are between about 50 micrometers and about 250 micrometers at their widest points. In some embodiments, at least 95% of the pores are between about 50 micrometers and about 150 micrometers at their widest points. In some embodiments, 100% of the pores are between about 10 micrometers and about 500 micrometers at their widest points.

In some embodiments, the ATM has a porosity of at least about 30%, at least about 50%, at least about 60%, at least about 70%, at least about 90%, at least about 95%, or at least about 99%. The pores may support ingrowth of cells, formation or remodeling of bone, cartilage and/or vascular tissue.

In some embodiments, the oxysterol is administered in an implant that is in solid or in semi-solid form. In various aspects, the oxysterol is (3S, 5S, 6S, 8R, 9S, 10R, 13S, 14S, 17S) 17-((S)-2-hydroxyoctan-2-yl)-10, 13-dimethylhexadecahydro-1H-cyclopenta[a]phenanthrene-3, 6-diol (Oxy133), Oxy149, Oxy153, Oxy154, Oxy155 or hydrates, solvates, amorphous forms, polymorphs or pharmaceutically acceptable salts thereof. In other aspects, the oxysterol includes polymorph Form A, polymorph Form B, polymorph Form C, polymorph Form D, polymorph Form E, polymorph Form F, polymorph Form G, polymorph Form H, polymorph Form I of Oxy133 or a mixture thereof as described in U.S. Ser. Nos. 15/082,695 and 15/374,610 incorporated herein by reference as if set forth in full.

The moldable form of the implant may have a pre-dosed viscosity in the range of about 1 to about 2000 centipoise (cps), 1 to about 200 cps, or 1 to about 100 cps. In various embodiments, the semi-solid or solid implant may comprise an acellular porcine collagen having a molecular weight (MW), as shown by the inherent viscosity (IV), from about 0.10 dL/g to about 1.2 dL/g or from about 0.20 dL/g to about 0.50 dL/g. Other IV ranges include but are not limited to about 0.05 to about 0.15 dL/g, about 0.10 to about 0.20 dL/g, about 0.15 to about 0.25 dL/g, about 0.20 to about 0.30 dL/g, about 0.25 to about 0.35 dL/g, about 0.30 to about 0.35 dL/g, about 0.35 to about 0.45 dL/g, about 0.40 to about 0.45 dL/g, about 0.45 to about 0.55 dL/g, about 0.50 to about 0.70 dL/g, about 0.55 to about 0.6 dL/g, about 0.60 to about 0.80 dL/g, about 0.70 to about 0.90 dL/g, about 0.80 to about 1.00 dL/g, about 0.90 to about 1.10 dL/g, about 1.0 to about 1.2 dL/g, about 1.1 to about 1.3 dL/g, about 1.2 to about 1.4 dL/g, about 1.3 to about 1.5 dL/g, about 1.4 to about 1.6 dL/g, about 1.5 to about 1.7 dL/g, about 1.6 to about 1.8 dL/g, about 1.7 to about 1.9 dL/g, or about 1.8 to about 2.1 dL/g.

In some embodiments, the ATM has a modulus of elasticity in the range of about $1 \times 10^2$ to about $6 \times 10^5$ dyn/cm$^2$, or $2 \times 10^4$ to about $5 \times 10^5$ dyn/cm$^2$, or $5 \times 10^4$ to about $5 \times 10^5$ dyn/cm$^2$. In some embodiments, the ATM is in lyophilized form.

In some embodiments, the ATM has a density of between about 1.6 g/cm$^3$, and about 0.05 g/cm$^3$. In some embodiments, the ATM has a density of between about 1.1 g/cm$^3$, and about 0.07 g/cm$^3$. For example, the density may be less than about 1 g/cm$^3$, less than about 0.7 g/cm$^3$, less than about 0.6 g/cm$^3$, less than about 0.5 g/cm$^3$, less than about 0.4 g/cm$^3$, less than about 0.3 g/cm$^3$, less than about 0.2 g/cm$^3$, or less than about 0.1 g/cm$^3$.

In some embodiments, the diameter or diagonal of the ATM can range from 1 mm to 50 mm. In some embodiments, the diameter or diagonal of the ATM can range from 1 mm to 30 mm, or 5 mm to 10 mm which is small enough to fit through an endoscopic cannula, but large enough to minimize the number of matrices needed to fill a large bone defect (e.g., osteochondral defect). In some embodiments, at the time of surgery, the ATM can be molded by the surgeon to the desired shape to fit the tissue or bone defect.

In some embodiments, the porous interior can hold the oxysterol within the ATM and because the interior is porous, the oxysterol is evenly distributed throughout the ATM when oxysterol is incorporated into the ATM, as discussed herein.

In some embodiments, oxysterol will be held within the interior of the ATM and released into the environment surrounding the ATM (e.g., bone defect, osteochondral defect, etc.) as the ATM degrades over time.

In some embodiments, the ATM may be seeded with harvested bone cells and/or bone tissue, such as for example, cortical bone, autogenous bone, allogenic bones and/or xenogeneic bone. In some embodiments, the ATM may be seeded with harvested cartilage cells and/or cartilage tissue (e.g., autogenous, allogenic, and/or xenogeneic cartilage tissue). For example, before insertion into the target tissue site, the ATM can be wetted with the graft bone tissue/cells, usually with bone tissue/cells aspirated from the patient, at a ratio of about 3:1, 2:1, 1:1, 1:3 or 1:2 by volume. The bone tissue/cells are permitted to soak into the ATM provided, and the ATM may be kneaded by hand or machine, thereby obtaining a pliable and cohesive consistency that may subsequently be packed into the bone defect. In some embodiments, the ATM provides a malleable, non-water soluble carrier that permits accurate placement and retention at the implantation site. In some embodiments, the harvested bone and/or cartilage cells can be mixed with the oxysterol and seeded in the interior of the ATM.

Acellular Tissue Matrix (ATM)

As used herein, an "acellular tissue matrix" (ATM) is a tissue-derived structure that is made from any of a wide range of collagen-containing tissues by removing all, or substantially all, viable cells and also all detectable dead cells, subcellular components and/or debris generated by dead or dying cells. In various aspects, an "acellular tissue matrix" is a matrix that: (a) is made from any of a wide range of collagen-based tissue; (b) is acellular; and (c) retains the biological and structural functions possessed by the native tissue or organ from which it was made. As used herein, an ATM lacking "substantially all viable cells" is an ATM in which the concentration of viable cells is less than 1% (for example, less than: 0.1%; 0.01%; 0.001%; 0.0001%; 0.00001%; or 0.000001%) of that in the tissue or organ from which the bone material was made. An ATM "substantially lacking dead cells and/or cell debris" is one that contains less than 10% (for example, less than: 8%; 5%; 1%; 0.1%; 0.001%; 0.0001%; or less) of the dead cells and/or cell debris present in the bone material following a cell removal process.

Biological functions retained by ATM include cell recognition and cell binding as well as the ability to support cell spreading, cell proliferation, and cell differentiation. Such functions are provided by undenatured collagenous proteins (e.g., Type I collagen) and a variety of non-collagenous molecules (e.g., proteins that serve as ligands for either molecules such as integrin receptors, molecules with high charge density such as glycosaminoglycans (e.g., hyaluronan) or proteoglycans, or other adhesions). Structural functions retained by useful acellular matrices include maintenance of histological architecture, maintenance of the three-dimensional array of the components of the tissue and physical characteristics such as strength, elasticity, and durability, defined porosity, and retention of macromolecules. The efficiency of the biological functions of an ATM can be measured, for example, by its ability to support cell proliferation and is at least 50% (e.g., at least: 50%; 60%; 70%; 80%; 90%; 95%; 98%; 99%; 99.5%; 100%; or more than 100%) of those of the native tissue or organ from which the ATM is made. In addition, the integrity of the basement membrane in the ATM, as measured by electron microscopy and/or immunohistochemistry, is at least 70% of that of the native tissue or organ from which the ATM is made.

As long as the above-described properties are retained by the ATM, the bone material can be produced from any mammal collagen-based tissue (e.g., dermis, fascia, umbilical cords, placentae, cardiac valves, ligaments, tendons, vascular tissue (arteries and veins such as saphenous veins, neural connective tissue, or ureters). In some aspects, the tissues in which these allografts can be placed include essentially any tissue that can be remodeled by invading or infiltrating cells. Relevant tissues include skeletal tissues such as bone, cartilage, ligaments, fascia, and tendon. Other tissues in which any of the above acellular tissue matrix can be placed include, without limitation, skin, gingiva, dura, myocardium, vascular tissue, neural tissue, striated muscle, smooth muscle, bladder wall, ureter tissue, intestine, and urethra tissue.

In various embodiments, the acellular tissue matrix material may comprise any collagen-containing tissue material of mammal origin, human or animal. The acellular tissue matrix material may be a tissue comprising predominantly Type I collagen. In other aspects, starting materials include dermis and tendons. In some embodiments, porcine tissue materials are processed to provide the collagenous material, although it will be understood that other mammalian sources may alternatively be employed, such as, for example, primates, cows, sheep, goats or horses. An example of an acellular porcine tissue matrix useful for the implant of this application is Permacol®. Permacol® is derived from porcine dermis which has undergone the removal of cellular components and genetic material. The remaining extracellular acellular tissue matrix (ATM), primarily collagen is then crosslinked to form an ATM which contains 20% collagen in 80% saline. Permacol® has been found to induce minimal foreign body rejection and to be resistant to biodegradation by native collagenases.

Depending upon the starting material, the particles of collagen may contain a proportion of elastin. Thus, the particles, and the coherent collagenous materials formed therefrom, consist essentially of collagen optionally with small proportions of elastin.

The particles of acellular collagen may be formed using any suitable process. The original collagen fiber architecture and molecular ultrastructure of the natural tissue material must be retained in the particles. The collagenous tissue is neither solubilized nor denatured in the process, so its natural fiber structure is maintained. All that is required is that the steps used in their production result in matrices with the biological and structural properties described above. Useful methods of production include those described in U.S. Pat. Nos. 5,397,353 and 6,936,271, U.S. Published Pat. Application Nos. 2013/0045923 and 2013/0267465, and EP1112096, all of which are incorporated herein by reference in their entirety.

Thus, freshly cut natural tissue material may be treated to remove therefrom substantially all lipids and lipid residues and thereafter treated to remove non-fibrous tissue proteins and cellular elements. The lipid extraction may be achieved by solvent extraction using an organic solvent, such as acetone. Other non-limiting examples of suitable solvents include non-aqueous solvents such as ethanol and ether.

Non-fibrous tissue proteins include glycoproteins, proteoglycans, globular proteins and the like, such as components of extracellular ATM. Cellular elements include antigenic proteins and enzymes and other cellular debris arising from the processing conditions. These portions of the natural tissue material may be removed by treatment with a proteolytic enzyme, such as trypsin. It has previously been found that above 20° C. treatment with trypsin can, in some cases, result in an alteration of the collagen fiber structure leading to a lower physical strength. Moreover, low temperatures discourage the growth of microorganisms in the preparation. It is therefore useful to carry out the treatment with trypsin at a temperature below 20° C. Moreover, trypsin is more stable below 20° C. and lower amounts of it may be required. Any suitable trypsin concentration may be used, for instance a concentration within the range of around 0.01 g/l to 25 g/l. It has been found that good results can be obtained using about 2.5 g/l trypsin. Further treatments may optionally be carried out, such as treatment with one or more additional enzymes, for example a carbohydrate-splitting enzyme.

The resulting collagenous material is then reduced to particles, care being taken to ensure that the size reduction is not associated with a degradation of the original collagen fiber architecture and molecular ultrastructure of the starting material. The particles may be produced by grinding or milling using, for example, a ball or hammer mill, which may be cooled to an appropriate temperature. The sheet material may be cut into small pieces prior to milling. Milling may be carried out in dry form (less than 10% moisture content) or in frozen hydrated form (20-80% moisture content).

The acellular collagen particles may be of any suitable size. In some embodiments, the acellular collagen particles have a mean diameter within the range of from around 5 µm to around 1000 µm, and in other embodiments, from around 50 µm to around 500 µm. Good results have been achieved using acellular collagen particles with a mean diameter of approximately 150 µm.

In brief, the steps involved in the production of an ATM include harvesting the tissue from a donor (e.g., a human cadaver or any of the above-listed mammals, including porcine dermis), chemical treatment so as to stabilize the tissue and avoid biochemical and structural degradation together with, or followed by, cell removal under conditions which similarly preserve biological and structural function. The bone material can optionally be treated with a cryopreservation agent and cryopreserved and, optionally, freeze-dried, again under conditions necessary to maintain the described biological and structural properties of the ATM. After freezing or freeze drying, the tissue can be fragmented, for example, pulverized or micronized to produce a particulate ATM under similar function-preserving conditions. All steps are generally carried out under aseptic sterile conditions.

An exemplary method of producing ATM, which is described in greater detail in U.S. Pat. No. 5,397,353, contains the following steps: (a) freshly cut dermis is extracted with acetone with one or more changes; (b) the dermis is placed in buffer or saline solution to remove the acetone; (c) the dermis is then subjected to digestion with trypsin solution pH 7.0 to 9.0 to remove antigenic proteins and cellular elements such as hair follicles and sweat glands; (d) optionally the tissue may be treated with a carbohydrate-splitting enzyme such as amylase, hyaluronidase or neuramidase to remove antigenic polysaccharides and mucopolysaccharides; (e) the purified tissue is stabilized by treatment with a diisocyanate, for example, hexane diisocyanate as a 0.1% solution in acetone; (f) two further washes with acetone; (g) rinse with buffer or saline; (h) store in presence of a bactericide or sterilize with gamma irradiation; and (i) pack under sterile conditions. According to this procedure, a non-resorbable, substantially non-antigenic collagenous fibrous tissue preparation of human or animal tissue origin is provided, which is suitable for homo- or heterotransplantation as a permanent repair for bone injuries, which preparation retains the natural structure and original architecture of the human or animal tissue, is substantially free of non-fibrous tissue proteins and glycoproteins, is substantially free of cellular elements, is substantially free of lipids and lipid residues and is non-cytotoxic, wherein the preparation is capable when implanted of being recolonized by host cells (e.g., osteoblasts, osteoclasts, etc.) and revascularized. In addition, a non-resorbable, substantially non-antigenic collagenous fibrous tissue preparation is also substantially free of antigenic polysaccharides and mucopolysaccharides.

According to a further aspect of the present application there is provided a process for the manufacture of an acellular collagenous material from a natural tissue material, wherein the process comprises the steps of: (i) treating the natural tissue material with an organic solvent; (ii) treating the natural tissue material with a proteolytic enzyme, so as to provide a treated material that is substantially free of non-fibrous tissue proteins, cellular elements and lipids or lipid residues and displays original collagen fiber architecture and molecular ultrastructure of the natural tissue material from which it is derived; (iii) reducing the treated material to a plurality of collagen particles comprising fragments of collagen fibers; and (iv) freeze drying the collagen particles in suspension in a freeze-drying suspension medium, wherein the process, in some aspects, excludes swelling of the collagen particles with acid and/or alkali.

According to another aspect of this application, there is provided a process for the manufacture of an acellular collagenous material from a plurality of collagen particles, the collagen particles comprising fragments of collagen fibers and being derived from a treated material, the treated material having been produced from a natural tissue material by treatment with an organic solvent and with a proteolytic enzyme so as to provide a material that is substantially free of non-fibrous tissue proteins, cellular elements and lipids or lipid residues and displays original collagen fiber architecture and molecular ultrastructure of the natural tissue material, wherein the process comprises the step of freeze drying the collagen particles in suspension in a freeze-drying suspension medium and wherein the process excludes swelling of the collagen particles with acid and/or alkali.

In some embodiments, tissue will infiltrate the bone material to a degree of about at least 50 percent within about 1 month to about 6 months after implantation of the ATM. In other embodiments, about 75 percent of the bone material will be infiltrated by tissue within about 2-3 months after implantation of the ATM. In some cases, the ATM will be substantially about 90 percent or more, submerged in or enveloped by tissue within about 6 months after implantation of the ATM. In other cases, the ATM will be completely submerged in or enveloped by tissue within about 9-12 months after implantation.

In some aspects, the implant of this application can include an oxysterol uniformly disposed in an ATM, wherein the ATM comprises acellular collagen from other sources, e.g., primates, bovine, ovine or piscine, in some cases crosslinked, while in others non-crosslinked. This kind of ATM can be placed in a syringe for delivery to a surgical site or can be lyophilized for rehydration at a surgical site. Useful acellular tissue matrices prepared from sources other than porcine collagen, as described above, can also be utilized to form an implant wherein an oxysterol is uniformly disposed (e.g., dispersed). Implants prepared from these ATMs can also include other bone material including inorganic particles with or without binding or swelling materials. As with ATMs containing porcine collagen, in these ATMs, the collagen can be crosslinked or non-crosslinked. Implants including ATMs prepared from acellular non-porcine collagen can be delivered in the same way as ATMs containing acellular porcine collagen, namely through a syringe or can be lyophilized and then rehydrated for delivery to a surgical site.

In some embodiments, the implant prepared from a sheet of substantially non-antigenic collageneous fibrous tissue preparation described above can be derived from porcine dermis. In some embodiments, the sheet of fibrous acellular collagenous tissue derived from porcine dermis can be cross-linked by means of a polyisocyanate, which in some case, is hexamethylene diisocyanate (HMDI). A product useful for the implant described in this application is Permacol®, a biological material prepared from porcine dermis and available as a paste. Porcine dermis is a good source of acellular collagen as it supports host cell infiltration and revascularization. Since Permacol® requires minimum rehydration, an implant containing Permacol® and an oxysterol can be prepared in only 30 seconds. Permacol® is typically crosslinked with diisocyanate which renders it fairly resistant to enzymatic degradation.

In other embodiments, there is provided an implant which comprises a biocompatible carrier having dispersed therein solid or semi-solid particles of acellular collagenous material derived from a natural tissue material including porcine dermis, wherein the acellular collagenous material preserves the original fiber architecture and molecular ultrastructure of the natural tissue material from which it is derived, wherein the acellular collagenous material is substantially free of non-fibrous tissue proteins, glycoproteins, cellular elements, lipids or lipid residues, wherein the acellular collagenous material is non-cytotoxic, wherein the implant composition is capable of use as a component of a paste, gel or an injectable solution, and wherein the particles of acellular collagenous material have a particle size within the range of approximately 50 microns to approximately 500 microns.

In other embodiments, the particles of acellular collagenous material have a particle size distribution wherein the particle sizes of at least 50 percent of the particles are within 35 percent of the average particle size, can be free of antigenic polysaccharides and mucopolysaccharides, and can be substantially free of antigenic polysaccharides and mucopolysaccharides. In various embodiments, the acellular collagenous material contains a proportion of elastin. In other aspects, the acellular collagenous material is cross-linked. In certain implementations, the biocompatible carrier is at least one of saline, glycerol, a dextran solution, a non-toxic antigenic viscous polysaccharide or a combination thereof. In certain aspects, the acellular collagenous material comprises approximately 10 percent by weight to approximately 90 percent by weight of the implant composition.

In some embodiments, the ATM comprises acellular collagen-containing biomaterials which, when placed in a bone defect, provide scaffolding around which the patient's new bone and/or cartilage will grow, gradually replacing the carrier ATM as the target site heals. Examples of suitable carrier matrices may include, but are not limited to, the MasterGraft® ATM produced by Medtronic Sofamor Danek, Inc., Memphis, Tenn.; MasterGraft® Putty produced by Medtronic Sofamor Danek, Inc., Memphis, Tenn.; Absorbable Collagen Sponge ("ACS") produced by Integra LifeSciences Corporation, Plainsboro, N.J.; bovine skin collagen fibers coated with hydroxyapatite, e.g., Healos® marketed by Johnson & Johnson, USA; collagen sponges, e.g., Hemostagene® marketed by Coletica S A, France, or e.g., Helisat® marketed by Integra Life Sciences Inc., USA; and Collagraft® Bone Graft ATM produced by Zimmer Holdings, Inc., Warsaw, Ind.

In some embodiments, the acellular collagen contains both soluble acellular collagen and insoluble acellular collagen fibers. The soluble acellular collagen and insoluble acellular collagen fibers can first be prepared separately, and then combined. Both the soluble acellular collagen and the insoluble acellular collagen fibers can be derived from a variety of sources, including human, bovine, ovine, piscine, or porcine sources.

In certain embodiments, the acellular collagen ATM includes moldable compositions that include the insoluble acellular collagen fibers at a level of 0.04 g/cc to 0.1 g/cc of the ATM, and soluble collagen at a level of 0.01 g/cc to 0.08 g/cc of the ATM. In other embodiments, such compositions include insoluble acellular collagen fibers at a level of about 0.05 to 0.08 g/cc in the ATM, and soluble acellular collagen at a level of about 0.02 to about 0.05 g/cc in the ATM. In general, the ATM will include insoluble acellular collagen fibers in an amount (percent by weight) that is at least equal to or greater than the amount of soluble acellular collagen, to contribute beneficially to the desired handling and implant properties of the ATM material. In some embodiments, the acellular collagenous ATM will include insoluble acellular collagen fibers and soluble acellular collagen present in a weight ratio of 4:1 to 1:1, in some cases, from about 75:25 to about 60:40. In other embodiments, the acellular collagen ATM may include the insoluble acellular collagen fibers and soluble acellular collagen in a weight ratio of about 75:25 to about 65:35, and in one embodiment about 70:30.

In some embodiments, the acellular collagen ATM comprises acellular porcine collagen and/or a non-polymeric material. In some embodiments, the acellular collagen ATM may include a biodegradable biopolymer that may provide immediate release, or sustained release of the oxysterol. For example, the acellular porcine collagen ATM may comprise polyether ether ketone (PEEK). In some embodiments, the acellular collagen ATM may comprise one or more of poly (alpha-hydroxy acids), polyglycolide (PG), polyethylene glycol (PEG), conjugates of poly (alpha-hydroxy acids), polyorthoesters (POE), polyaspirins, polyphosphagenes, collagen, hydrolyzed collagen, gelatin, hydrolyzed gelatin, fractions of hydrolyzed gelatin, elastin, starch, pre-gelatinized starch, hyaluronic acid, chitosan, alginate, albumin, fibrin, vitamin E analogs, such as alpha tocopheryl acetate, d-alpha tocopheryl succinate, D,L-lactide, or L-lactide, caprolactone, dextrans, vinylpyrrolidone, polyvinyl alcohol (PVA), PVA-g-PLGA, PEGT-PBT copolymer (polyactive), methacrylates, PEO-PPO-PAA copolymers, PLGA-PEO-PLGA, PEG-PLG, PLA-PLGA, poloxamer 407, PEG-PLGA-PEG triblock copolymers, POE, SAIB (sucrose acetate isobutyrate), polydioxanone, methylmethacrylate (MMA), MMA and N-vinylpyyrolidone, polyamide, oxycellulose, copolymer of glycolic acid and trimethylene carbonate, polyesteramides, polyether ether ketone, polymethylmethacrylate, silicone, hyaluronic acid, chitosan, or combinations thereof.

In some embodiments, the implant may not be fully biodegradable. For example, the device may comprise polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon device, glass device, plastics, ceramics, methacrylates, poly (N-isopropylacrylamide), PEO-PPO-PEO (pluronics) or combinations thereof. In some embodiments, these types of matrices may need to be removed after a certain amount of time.

In some embodiments, the implant comprises at least one acellular porcine collagen comprising one or more of poly (lactide-co-glycolide) (PLGA), polylactide (PLA), polyglycolide (PGA), D-lactide, D,L-lactide, L-lactide, D,L-lactide-co-ε-caprolactone, L-lactide-co-ε-caprolactone, D,L-lactide-co-glycolide-co-ε-caprolactone, poly (D,L-lactide-co-caprolactone), poly(L-lactide-co-caprolactone), poly (D-lactide-co-caprolactone), poly (D,L-lactide), poly (D-lactide), poly (L-lactide), poly (esteramide) or a combination thereof. In some embodiments, the oxysterol is encapsulated in an acellular porcine collagen.

In some embodiments, the ATM comprises one or more polymers (e.g., PLA, PLGA) having a MW of from about 15,000 to about 150,000 Da or from about 25,000 to about 100,000 Da.

In some embodiments, the implant comprises at least one biodegradable material in a wt. % of from about 99.5%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 76%, 75%, 74%, 73%, 72%, 71%, 70%, 65%, 60%, 55%, 50%, 45%, 35%, 25%, 20%, 15%, 10%, or to about 5% based on the total weight of the ATM or the implant. In some embodiments, the acellular porcine collagen comprises a range of from about 0.1% to about 20 based on the total weight of the ATM or the implant. In some embodiments, the acellular porcine collagen comprises a range of from about 0.1% to about 15% based on the total weight of the ATM or the implant. In some embodiments, the acellular porcine collagen comprises from about 14%, 13%, 12%, 11%, 9%, 8%, 7%, 6%, or to about 5% based on the total weight of the ATM or the implant.

In some embodiments, the acellular porcine collagen is present in the ATM in an amount of from about 0.01 wt. % to about 50 wt. % or from about 8.0 wt. % to about 50 wt. % of the ATM. In some embodiments, the acellular porcine collagen is present in an amount of from about 0.1 wt. % to about 10 wt. %, from about 10 wt. % to about 20 wt. %, from about 20 wt. % to about 30 wt. %, from about 30 wt. % to about 40 wt. %, or from about 40 wt. % to about 50 wt. %.

Mannitol, trehalose, dextran, mPEG and/or PEG may be used as a plasticizer for the polymer. In some embodiments, the polymer and/or plasticizer may also be coated on the implant to provide the desired release profile. In some embodiments, the coating thickness may be thin, for example, from about 5, 10, 15, 20, 25, 30, 35, 40, 45 or 50 microns to thicker coatings 60, 65, 70, 75, 80, 85, 90, 95, 100 microns to delay release of the oxysterol from the implant. In some embodiments, the range of the coating on the implant ranges from about 5 microns to about 250 microns or 5 microns to about 200 microns to delay release from the implant.

Compression resistance may be desirable for many tissue engineering applications such as tibial plateau fractures, acetabular defects, long bone comminuted fractures, oral maxillofacial defects, spinal fusions, and cartilage subchondral defects. Compression resistant collagen matrices will help facilitate adequate volumes of newly formed bone.

In some embodiments, the ATM is compression resistant where the ATM resists reduction in size or an increase in density when a force is applied as compared to collagen matrices without the bone material disposed in it. In various embodiments, the acellular collagen ATM resists compression by 10%, 15%, 20%, 25%, 30%, 35%, 40%, 45%, 50%, 55%, 60%, 65%, 70%, 75%, 80%, 85%, 90%, 95%, or more in one or all directions when a force is applied to the ATM.

Bone Material

In some embodiments, the implant can contain demineralized bone material disposed therein. The demineralized bone material can comprise demineralized bone powder, chips, triangular prisms, spheres, cubes, cylinders, shards, fibers or other shapes having irregular or random geometries. These can include, for example, "substantially demineralized," "partially demineralized," or "fully demineralized" cortical and cancellous bone. These also include surface demineralization, where the surface of the bone construct is substantially demineralized, partially demineralized, or fully demineralized, yet the body of the bone construct is fully mineralized. In some embodiments, the acellular tissue matrix may comprise some fully mineralized bone material. The configuration of the bone material can be obtained by milling, shaving, cutting or machining whole bone as described in for example U.S. Pat. No. 5,899,939. The entire disclosure is herein incorporated by reference into the present disclosure.

In some embodiments, the bone material can comprise elongated demineralized bone fibers having an average length to average thickness ratio or aspect ratio of the fibers from about 50:1 to about 1000:1. In overall appearance, the elongated demineralized bone fibers can be round, spherical, granular, elongated, powders, chips, fibers, cylinders, threads, narrow strips, thin sheets, or a combination thereof. The elongated demineralized bone fibers can be substantially linear in appearance or they can be coiled to resemble springs. In some embodiments, the elongated demineralized bone fibers are of irregular shapes including, for example, linear, serpentine or curved shapes. The elongated bone fibers can be demineralized, however some of the original mineral content may be retained when desirable for a particular embodiment. In some embodiments, the bone material comprises elongated demineralized bone fibers and chips. In some embodiments, the bone material comprises fully demineralized fibers and surface demineralized chips. In some embodiments, the ratio of fibers to chips or powders is from about 5, 10, 15, 20, 25, 30, 35, 40, or 45 fibers to about 30, 35, 40, 45, 50, 55, 60, 65, or 70 chips.

In some embodiments, the bone material comprises demineralized bone ATM (DBM) fibers and demineralized bone ATM chips in a 30:60 ratio. In some embodiments, the bone material comprises demineralized bone ATM fibers and demineralized bone ATM chips in a ratio of 25:75 to about 75:25 fibers to chips.

In some embodiments, the demineralized bone ATM may be seeded with harvested bone cells and/or bone tissue, such as for example, cortical bone, autogenous bone, allogenic bones and/or xenogeneic bone. In some embodiments, the DBM ATM may be seeded with harvested cartilage cells and/or cartilage tissue (e.g., autogenous, allogenic, and/or xenogeneic cartilage tissue). For example, before insertion into the target tissue site, the DBM ATM can be wetted with the graft bone tissue/cells, usually with bone tissue/cells aspirated from the patient, at a ratio of about 3:1, 2:1, 1:1, 1:3 or 1:2 by volume. The bone tissue/cells are permitted to soak into the DBM ATM provided, and the ATM may be kneaded by hand or machine, thereby obtaining a pliable and cohesive consistency that may subsequently be packed into the bone defect. In some embodiments, the DBM ATM provides a malleable, non-water soluble carrier that permits accurate placement and retention at the implantation site. In some embodiments, the harvested bone and/or cartilage cells can be mixed with the Oxy133 and seeded in the interior of the ATM.

In some embodiments, the bone material further comprises mineral particles, such as, for example, ceramics. In some embodiments, the particles in the implant comprise a resorbable ceramic, bone, synthetic degradable polymer, hyaluronic acid, chitosan or combinations thereof.

In some embodiments, the particles comprise cortical, cancellous, and/or cortico-cancellous, allogenic, xenogeneic or transgenic bone tissue. In some embodiments, the mineral particles comprise, consist essentially of or consist of bone powder, demineralized bone powder, porous calcium phosphate ceramics, hydroxyapatite, tricalcium phosphate, bioactive glass or combinations thereof.

In some embodiments, the bone material may comprise a resorbable ceramic (e.g., hydroxyapatite, tricalcium phosphate, bioglasses, calcium sulfate) tyrosine-derived polycarbonate poly (DTE-co-DT carbonate), in which the pendant group via the tyrosine—an amino acid—is either an ethyl ester (DTE) or free carboxylate (DT) or combinations thereof.

In some embodiments, the bone material may contain an inorganic material, such as an inorganic ceramic and/or bone substitute material. Exemplary inorganic materials or bone substitute materials include but are not limited to aragonite, dahlite, calcite, brushite, amorphous calcium carbonate, vaterite, weddellite, whewellite, struvite, urate, ferrihydrate, francolite, monohydrocalcite, magnetite, goethite, dentin, calcium carbonate, calcium sulfate, calcium phosphosilicate, sodium phosphate, calcium aluminate, calcium phosphate, hydroxyapatite, alpha-tricalcium phosphate, dicalcium phosphate, β-tricalcium phosphate, tetracalcium phosphate, amorphous calcium phosphate, octacalcium phosphate, BIOGLASS™ fluoroapatite, chlorapatite, magnesium-substituted tricalcium phosphate, carbonate hydroxyapatite, substituted forms of hydroxyapatite (e.g., hydroxyapatite derived from bone may be substituted with other ions such as fluoride, chloride, magnesium sodium, potassium, etc.), or combinations or derivatives thereof.

In some embodiments, by including inorganic ceramics, such as for example, calcium phosphate in the implant, this will act as a local source of calcium and phosphate to the cells attempting to deposit new bone. The inorganic ceramic also provides compression resistance and load bearing characteristics to the implant.

In some embodiments, the mineral particles in the implant comprise tricalcium phosphate and hydroxyapatite in a ratio of about 80:20 to about 90:10. In some embodiments, the mineral particles in the implant comprise tricalcium phosphate and hydroxyapatite in a ratio of about 70:30 to about 95:5. In some embodiments, the mineral particles in the implant comprise tricalcium phosphate and hydroxyapatite in a ratio of about 85:15.

In some embodiments, the bone material comprises mineral particles that offer compression resistance. In some embodiments, the mineral particles (e.g., ceramic) comprise at least from about 10%, 15%, 20%, 25%, 30%, 35%, 40%, 45%, 50%, 55%, 60%, 65%, 70%, 75%, 80%, 85%, 90%, or to about 95% by weight of the ATM. In some embodiments, the particles are predominantly any shape (e.g., round, spherical, elongated, powders, chips, fibers, cylinders, etc.).

In some embodiments, the bone material comprises mineral particles in an amount of about 0.1 wt. % to about 95 wt. % of the ATM. In some embodiments, the bone material comprises mineral particles in an amount of about 50 wt. % to about 80 wt. % of the ATM. In some embodiments, the ATM comprises from about 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, or to about 79% by weight of the ATM.

In some embodiments, the mineral particles are present in an amount of about 0.1 wt. % to about 30 wt. % of the bone material. In some embodiments, the mineral particles are present in an amount between about 0.01 wt. % to about 50 wt. % of the ATM. In some embodiments, the mineral particles are present in an amount between about 7.0 wt. % to about 50 wt. % of the ATM. In some embodiments, the mineral particles are present in an amount of about 0.1 wt.

% to about 10 wt. %, about 10 wt. % to about 20 wt. %, about 20 wt. % to about 30 wt. %, about 30 wt. % to about 40 wt. %, or about 40 wt. % to about 50 wt. %.

In some embodiments, the porosity of the particles comprises from 0 to 50%, in some embodiments, the porosity of the particles comprises 5% to 25%. In some embodiments, the particles are not entangled with each other but contact each other and portions of each particle overlap in the bone material to provide compression resistance. In some embodiments, at least 50%, 55%, 60%, 65%, 70%, 75%, 80%, 85%, 90%, 95%, or more of the particles overlap each other in the ATM.

In some embodiments, the particles are randomly distributed throughout the ATM. In other embodiments, the particles are uniformly or evenly distributed throughout the ATM. In some embodiments, the particles may be dispersed in the ATM using a dispersing agent. In other embodiments, the particles may be stirred in the polymer and the mechanical agitation will distribute the particles in the ATM until the desired distribution is reached (e.g., random or uniform).

In some embodiments, the bone material may be mixed with one or more therapeutic agents, for example, an anti-inflammatory agent, an analgesic agent, an osteoinductive growth factor, an antimicrobial agent or a combination thereof. Osteoinductive agents include one or more members of the family of Bone Morphogenetic Proteins ("BMPs"). BMPs are a class of proteins thought to have osteoinductive or growth-promoting activities on endogenous bone tissue, or function as pro-collagen precursors. Known members of the BMP family include, but are not limited to, BMP-1, BMP-2, BMP-3, BMP-4, BMP-5, BMP-6, BMP-7, BMP-8, BMP-9, BMP-10, BMP-11, BMP-12, BMP-13, BMP-14 (GDF-5), BMP-15, BMP-16, BMP-17, BMP-18 as well as polynucleotides or polypeptides thereof, as well as mature polypeptides or polynucleotides encoding the same.

BMPs utilized as osteoinductive agents comprise one or more of BMP-1; BMP-2; BMP-3; BMP-4; BMP-5; BMP-6; BMP-7; BMP-8; BMP-9; BMP-10; BMP-11; BMP-12; BMP-13; BMP-15; BMP-16; BMP-17; or BMP-18; as well as any combination of one or more of these BMPs, including full length BMPs or fragments thereof, or combinations thereof, either as polypeptides or polynucleotides encoding the polypeptide fragments of all of the recited BMPs. The isolated BMP osteoinductive agents may be administered as polynucleotides, polypeptides, full length protein or combinations thereof.

Indeed, the osteoinductive factors are the recombinant human bone morphogenetic proteins (rhBMPs) because they are available in unlimited supply and do not transmit infectious diseases. In some embodiments, the bone morphogenetic protein is rhBMP-2, rhBMP-4, rhBMP-7, or heterodimers thereof.

Recombinant BMP-2 can be used at a concentration of about 0.4 mg/mL to about 10.0 mg/mL, in some cases about 1.5 mg/mL. However, any bone morphogenetic protein is contemplated including bone morphogenetic proteins designated as BMP-1 through BMP-18. BMPs are available from Wyeth, Cambridge, Mass. and the BMPs and genes encoding them may also be prepared by one skilled in the art as described in U.S. Pat. No. 5,187,076 to Wozney et al.; U.S. Pat. No. 5,366,875 to Wozney et al.; U.S. Pat. No. 4,877,864 to Wang et al.; U.S. Pat. No. 5,108,922 to Wang et al.; U.S. Pat. No. 5,116,738 to Wang et al.; U.S. Pat. No. 5,013,649 to Wang et al.; U.S. Pat. No. 5,106,748 to Wozney et al.; PCT Patent Nos. WO93/00432 to Wozney et al.; WO94/26893 to Celeste et al.; and WO94/26892 to Celeste et al. All osteoinductive factors are contemplated whether obtained as above or isolated from bone. Methods for isolating bone morphogenetic protein from bone are described, for example, in U.S. Pat. No. 4,294,753 to Urist and Urist et al., 81 PNAS 371, 1984.

The bone material may include or be mixed with one or more members from the TGF-β superfamily. For example, the ATM may include AMH, ARTN, GDF1, GDF10, GDF11, GDF15, GDF2, GDF3, GDF3A, GDF5, GDF6, GDF7, GDF8, GDF9, GDNF, INHA, INHBA, INHBB, INHBC, INHBE, LEFTY1, LEFTY2, MSTN, NODAL, NRTN, PSPN, TGFB1, TGFB2, TGFB3, FGF, basic FGF, VEGF, insulin-like growth factor, EGF, PDGF, nerve growth factor or combinations thereof.

The bone material may include or be mixed with a therapeutic agent including, but not limited to, IL-1 inhibitors, such as Kineret® (anakinra), which is a recombinant, non-glycosylated form of the human interleukin-1 receptor antagonist (IL-1Ra), or AMG108, which is a monoclonal antibody that blocks the action of IL-1. The bone material may include or be mixed with therapeutic agents including excitatory amino acids such as glutamate and aspartate, antagonists or inhibitors of glutamate binding to NMDA receptors, AMPA receptors, and/or kainate receptors. The bone material may include or be mixed with therapeutic agents to reduce inflammation including but not limited to interleukin-1 receptor antagonists, thalidomide (a TNF-α release inhibitor), thalidomide analogues (which reduce TNF-α production by macrophages), quinapril (an inhibitor of angiotensin II, which upregulates TNF-α), interferons such as IL-11 (which modulate TNF-α receptor expression), or aurin-tricarboxylic acid (which inhibits TNF-α).

The bone material may include or be mixed with a therapeutic agent including, but not limited to, an analgesic agent. Examples of analgesic agents include, but are not limited to, acetaminophen, tramadol, lidocaine, bupivacaine, ropivacaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, levorphanol, meperidine, methadone, morphine, nalbuphine, opium, oxycodone, papaveretum, pentazocine, pethidine, phenoperidine, piritramide, dextropropoxyphene, remifentanil, sufentanil, tilidine, tramadol, codeine, dihydrocodeine, meptazinol, dezocine, eptazocine, flupirtine or a combination thereof.

The bone material may include or be mixed with a therapeutic agent including, but not limited to, an anti-inflammatory agent. An example of an anti-inflammatory agent includes, but is not limited to, clonidine, sulindac, sulfasalazine, naroxyn, diclofenac, indomethacin, ibuprofen, flurbiprofen, ketoprofen, aclofenac, aloxiprin, aproxen, aspirin, diflunisal, fenoprofen, mefenamic acid, naproxen, phenylbutazone, piroxicam, meloxicam, salicylamide, salicylic acid, desoxysulindac, tenoxicam, ketorolac, clonidine, flufenisal, salsalate, triethanolamine salicylate, aminopyrine, antipyrine, oxyphenbutazone, apazone, cintazone, flufenamic acid, clonixeril, clonixin, meclofenamic acid, flunixin, colchicine, demecolcine, allopurinol, oxypurinol, benzydamine hydrochloride, dimefadane, indoxole, intrazole, mimbane hydrochloride, paranylene hydrochloride, tetrydamine, benzindopyrine hydrochloride, fluprofen, ibufenac, naproxol, fenbufen, cinchophen, diflumidone sodium, fenamole, flutiazin, metazamide, letimide hydrochloride, nexeridine hydrochloride, octazamide, molinazole, neocinchophen, nimazole, proxazole citrate, tesicam, tesimide, tolmetin, triflumidate, fenamates (mefenamic acid, meclofenamic acid), nabumetone, celecoxib, etodolac, nimesulide, apazone, gold, tepoxalin; dithiocarbamate, or a combination thereof.

Anti-inflammatory agents also include steroids, such as for example, 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, dexamethasone 21-acetate, dexamethasone 21-phosphate di-Na salt, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide or a combination thereof.

The bone material may include or be mixed with a therapeutic agent including, but not limited to, a statin. Examples of a useful statin includes, but is not limited to, atorvastatin, simvastatin, pravastatin, cerivastatin, mevastatin (see U.S. Pat. No. 3,883,140, the entire disclosure is herein incorporated by reference), velostatin (also called synvinolin; see U.S. Pat. Nos. 4,448,784 and 4,450,171 these entire disclosures are herein incorporated by reference), fluvastatin, lovastatin, rosuvastatin and fluindostatin (Sandoz XU-62-320), dalvastain (EP Appln. Publn. No. 738510 A2, the entire disclosure is herein incorporated by reference), eptastatin, pitavastatin, or pharmaceutically acceptable salts thereof or a combination thereof. In various embodiments, the statin may comprise mixtures of (+)R and (−)-S enantiomers of the statin. In various embodiments, the statin may comprise a 1:1 racemic mixture of the statin.

In some embodiments, the bone material can include an antimicrobial agent. In some embodiments, the antimicrobial agent can include one or more of triclosan, also known as 2,4,4'-trichloro-2'-hydroxydiphenyl ether, chlorhexidine and its salts, including chlorhexidine acetate, chlorhexidine gluconate, chlorhexidine hydrochloride, and chlorhexidine sulfate, silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine, polymyxin, tetracycline, aminoglycosides, such as tobramycin and gentamicin, rifampicin, bacitracin, neomycin, chloramphenicol, miconazole, quinolones such as oxolinic acid, norfloxacin, nalidixic acid, pefloxacin, enoxacin and ciprofloxacin, penicillins such as oxacillin and pipracil, nonoxynol 9, fusidic acid, cephalosporins, or combinations thereof.

Examples of antimicrobial agents include, by way of illustration and not limited to, acedapsone; acetosulfone sodium; alamecin; alexidine; amdinocillin; amdinocillin pivoxil; amicycline; amifloxacin; amifloxacin mesylate; amikacin; amikacin sulfate; aminosalicylic acid; aminosalicylate sodium; amoxicillin; amphomycin; ampicillin; ampicillin sodium; apalcillin sodium; apramycin; aspartocin; astromicin sulfate; avilamycin; avoparcin; azithromycin; azlocillin; azlocillin sodium; bacampicillin hydrochloride; bacitracin; bacitracin methylene disalicylate; bacitracin zinc; bambermycins; benzoylpas calcium; berythromycin; betamicin sulfate; biapenem; biniramycin; biphenamine hydrochloride; bispyrithione magsulfex; butikacin; butirosin sulfate; capreomycin sulfate; carbadox; carbenicillin disodium; carbenicillin indanyl sodium; carbenicillin phenyl sodium; carbenicillin potassium; carumonam sodium; cefaclor; cefadroxil; cefamandole; cefamandole nafate; cefamandole sodium; cefaparole; cefatrizine; cefazaflur sodium; cefazolin; cefazolin sodium; cefbuperazone; cefdinir; cefepime; cefepime hydrochloride; cefetecol; cefixime; cefmenoxime hydrochloride; cefmetazole; cefmetazole sodium; cefonicid monosodium; cefonicid sodium; cefoperazone sodium; ceforanide; cefotaxime sodium; cefotetan; cefotetan disodium; cefotiam hydrochloride; cefoxitin; cefoxitin sodium; cefpimizole; cefpimizole sodium; cefpiramide; cefpiramide sodium; cefpirome sulfate; cefpodoxime proxetil; cefprozil; cefroxadine; cefsulodin sodium; ceftazidime; ceftibuten; ceftizoxime sodium; ceftriaxone sodium; cefuroxime; cefuroxime axetil; cefuroxime pivoxetil; cefuroxime sodium; cephacetrile sodium; cephalexin; cephalexin hydrochloride; cephaloglycin; cephaloridine; cephalothin sodium; cephapirin sodium; cephradine; cetocycline hydrochloride; cetophenicol; chloramphenicol; chloramphenicol palmitate; chloramphenicol pantothenate complex; chloramphenicol sodium succinate; chlorhexidine phosphanilate; chloroxylenol; chlortetracycline bisulfate; chlortetracycline hydrochloride; cinoxacin; ciprofloxacin; ciprofloxacin hydrochloride; cirolemycin; clarithromycin; clinafloxacin hydrochloride; clindamycin; clindamycin hydrochloride; clindamycin palmitate hydrochloride; clindamycin phosphate; clofazimine; cloxacillin benzathine; cloxacillin sodium; chlorhexidine, cloxyquin; colistimethate sodium; colistin sulfate; coumermycin; coumermycin sodium; cyclacillin; cycloserine; dalfopristin; dapsone; daptomycin; demeclocycline; demeclocycline hydrochloride; demecycline; denofungin; diaveridine; dicloxacillin; dicloxacillin sodium; dihydrostreptomycin sulfate; dipyrithione; dirithromycin; doxycycline; doxycycline calcium; doxycycline fosfatex; doxycycline hyclate; droxacin sodium; enoxacin; epicillin; epitetracycline hydrochloride; erythromycin; erythromycin acistrate; erythromycin estolate; erythromycin ethylsuccinate; erythromycin gluceptate; erythromycin lactobionate; erythromycin propionate; erythromycin stearate; ethambutol hydrochloride; ethionamide; fleroxacin; floxacillin; fludalanine; flumequine; fosfomycin; fosfomycin tromethamine; fumoxicillin; furazolium chloride; furazolium tartrate; fusidate sodium; fusidic acid; ganciclovir and ganciclovir sodium; gentamicin sulfate; gloximonam; gramicidin; haloprogin; hetacillin; hetacillin potassium; hexedine; ibafloxacin; imipenem; isoconazole; isepamicin; isoniazid; josamycin; kanamycin sulfate; kitasamycin; levofuraltadone; levopropylcillin potassium; lexithromycin; lincomycin; lincomycin hydrochloride; lomefloxacin; lomefloxacin hydrochloride; lomefloxacin mesylate; loracarbef; mafenide; meclocycline; meclocycline sulfosalicylate; megalomicin potassium phosphate; mequidox; meropenem; methacycline; methacycline hydrochloride; methenamine; methenamine hippurate; methenamine mandelate; methicillin sodium; metioprim; metronidazole hydrochloride; metronidazole phosphate; mezlocillin; mezlocillin sodium; minocycline; minocycline hydrochloride; mirincamycin hydrochloride; monensin; monensin sodiumr; nafcillin sodium; nalidixate sodium; nalidixic acid; natainycin; nebramycin; neomycin palmitate; neomycin sulfate; neomycin undecylenate; netilmicin sulfate; neutramycin; nifuiradene; nifuraldezone; nifuratel; nifuratrone;

nifurdazil; nifurimide; nifiupirinol; nifurquinazol; nifurthiazole; nitrocycline; nitrofurantoin; nitromide; norfloxacin; novobiocin sodium; ofloxacin; onnetoprim; oxacillin and oxacillin sodium; oximonam; oximonam sodium; oxolinic acid; oxytetracycline; oxytetracycline calcium; oxytetracycline hydrochloride; paldimycin; parachlorophenol; paulomycin; pefloxacin; pefloxacin mesylate; penamecillin; penicillins such as penicillin g benzathine, penicillin g potassium, penicillin g procaine, penicillin g sodium, penicillin v, penicillin v benzathine, penicillin v hydrabamine, and penicillin v potassium; pentizidone sodium; phenyl aminosalicylate; piperacillin sodium; pirbenicillin sodium; piridicillin sodium; pirlimycin hydrochloride; pivampicillin hydrochloride; pivampicillin pamoate; pivampicillin probenate; polymyxin b sulfate; porfiromycin; propikacin; pyrazinamide; pyrithione zinc; quindecamine acetate; quinupristin; racephenicol; ramoplanin; ranimycin; relomycin; repromicin; rifabutin; rifametane; rifamexil; rifamide; rifampin; rifapentine; rifaximin; rolitetracycline; rolitetracycline nitrate; rosaramicin; rosaramicin butyrate; rosaramicin propionate; rosaramicin sodium phosphate; rosaramicin stearate; rosoxacin; roxarsone; roxithromycin; sancycline; sanfetrinem sodium; sarmoxicillin; sarpicillin; scopafungin; sisomicin; sisomicin sulfate; sparfloxacin; spectinomycin hydrochloride; spiramycin; stallimycin hydrochloride; stefimycin; streptomycin sulfate; streptonicozid; sulfabenz; sulfabenzamide; sulfacetamide; sulfacetamide sodium; sulfacytine; sulfadiazine; sulfadiazine sodium; sulfadoxine; sulfalene; sulfamerazine; sulfameter; sulfamethazine; sulfamethizole; sulfamethoxazole; sulfamonomethoxine; sulfamoxole; sulfanilate zinc; sulfanitran; sulfasalazine; sulfasomizole; sulfathiazole; sulfazamet; sulfisoxazole; sulfisoxazole acetyl; sulfisboxazole diolamine; sulfomyxin; sulopenem; sultamricillin; suncillin sodium; talampicillin hydrochloride; teicoplanin; temafloxacin hydrochloride; temocillin; tetracycline; tetracycline hydrochloride; tetracycline phosphate complex; tetroxoprim; thiamphenicol; thiphencillin potassium; ticarcillin cresyl sodium; ticarcillin disodium; ticarcillin monosodium; ticlatone; tiodonium chloride; tobramycin; tobramycin sulfate; tosufloxacin; trimethoprim; trimethoprim sulfate; trisulfapyrimidines; troleandomycin; trospectomycin sulfate; tyrothricin; vancomycin; vancomycin hydrochloride; virginiamycin; or combinations thereof.

The antimicrobial agent in the bone material can be an antiviral agent that can be mixed with the bone material. Antiviral agents can include, but are not limited to, vidarabine, acyclovir, famciclovir, valacyclovir, gancyclovir, valganciclovir, nucleoside-analog reverse transcriptase inhibitors (such as AZT (zidovudine), ddl (didanosine), ddC (zalcitabine), d4T (stavudine), and 3TC (lamivudine)), nevirapine, delavirdine, protease inhibitors (such as, saquinavir, ritonavir, indinavir, and nelfinavir), ribavirin, amantadine, rimantadine, neuraminidase inhibitors (such as zanamivir and oseltamivir), pleconaril, cidofovir, foscarnet, and/or interferons.

Expandable Phase

In some embodiments, the implant may comprise a material, such as, for example, a binder or expandable phase, to facilitate swelling of the implant. The expandable phase comprises polymers that swell upon taking in fluid (e.g., saline, water, bodily fluid), and thus increase the volume of the implant and which further holds the implant in position over time.

In some embodiments, the binder or expandable phase comprises a range of from about 0.1% to about 20% based on the total weight of the implant. In some embodiments, the binder or expandable phase comprises a range of from about 0.1% to about 10% based on the total weight of the implant. In some embodiments, the binder or expandable phase comprises from about 0.1%, 0.25%, 0.5%, 0.75%, 1%, 2%, 3%, 4%, 5%, 6%, 7%, 8%, 9% or to about 10% based on the total weight of the implant.

In some embodiments, the binder or expandable phase comprises polymers, monomers, starches, gums, poly(amino acids) or a combination thereof that swell upon contact with fluid (water, saline, body fluids). In various embodiments, the amount of swelling can range from about 5 to about 100 percent, from about 5 to about 40 percent, or from about 5 to about 20 percent. The time to reach maximum swelling can be varied depending on the location and desired property of the implant. In practice, the time to reach maximum swelling can occur within a period of 5 days, 3 days, 2 days or within a period of 24 hours.

Suitable swellable material may include without limitations, hydroxypropyl cellulose, hydroxypropyl methylcellulose, hydroxyethyl methylcellulose, carboxymethylcellulose, hydroxyethylcellulose and salts thereof, Carbopol, poly(hydroxyethylmethacrylate), poly(methoxyethylmethacrylate), gelatin, poly(methoxyethoxyethylmethacrylate), polymethylmethacrylate (PMMA), methylmethacrylate (MMA), polyvinyl alcohols, propylene glycol, PEG 200, PEG 300, PEG 400, PEG 500, PEG 550, PEG 600, PEG 700, PEG 800, PEG 900, PEG 1000, PEG 1450, PEG 3350, PEG 4500, PEG 8000 or combinations thereof. In some embodiments, the binder or expandable phase includes gelling polymers including but not limited to cellulosic polymers, vinyl polymers, such as polyvinylpyrrolidone; acrylic polymers and copolymers, such as acrylic acid polymer, methacrylic acid copolymers, ethyl acrylate-methyl methacrylate copolymers, or the like; or mixtures thereof.

In various implementations, the implant described in this application further comprises excipients, diluents, biodegradable polymers, swelling agents, growth factors, antibiotics, solubilizers, stabilizers, bulking agents, antioxidants or binders A non-limiting list of swellable materials which the binder or expandable phase may comprise include polyvinyl alcohol (PVA), PVA modified with hydrophilic co-monomers, e.g., AMPS, PVA modified with fast crosslinking groups, e.g., NAAADA, PVA modified with polyvinylpyrroline (PVP), carboxymethylcellulose, polyethylene glycol (PEG), poly(vinyl ether), co-polymers of PVA and PEG, polypropylene glycol (PPG), co-polymers of PEG and PPG, co-polymers of PVA or PPG, polyacrylonitrile, hydrocolloids, e.g. agar, alginates, collagen, elastin, chitin, chitosan, gelatin, sugar, mannitol, or the like. In various embodiments, the swellable material includes, for example, poly(N-isopropylacrylamide-co-acrylic acid)-poly(L-lactic acid) (NAL); poly(N-isopropyl acrylamide) (PNIPAM) grafted to other polymers such as carboxymethylcellulose (CMC) copolymers or polymers including block copolymers and end-functionalized polymers, composites or copolymers containing thermo-sensitive poly(2-ethoxyethyl vinyl ether) and/or poly(hydroxyethyl vinyl ether) and/or (EOVE200-HOVE400), whose sol-gel transition temperature is 20.5° C. The swellable material, in various embodiments, may be used to control release of the oxysterol into the tissue and/or the synovial space.

In some embodiments, the binder or expandable phase includes hyaluronic acid. In some embodiments, the binder or expandable phase includes glycosaminoglycans. Non-limiting examples of glycosaminoglycans include chondroitin sulfate, dermatan sulfate, keratin sulfate, heparin, heparin sulfate, and hyaluronan. In some embodiments, the binder or expandable phase includes mannitol, PEG, magnesium alginate or glycerol.

The polymers may be crosslinked or lightly crosslinked hydrophilic polymers. Although these polymers may be non-ionic, cationic, zwitterionic, or anionic, in various embodiments, the swellable polymers are cationic or anionic. In various embodiments, the swellable polymer may contain a multiplicity of acid functional groups, such as carboxylic acid groups, or salts thereof. Examples of such polymers suitable for use herein include those which are prepared from polymerizable, acid-containing monomers, or monomers containing functional groups which can be converted to acid groups after polymerization. Examples of such polymers also include polysaccharide-based polymers such as carboxymethyl starch and cellulose, and poly(amino acid) polymers such as poly(aspartic acid). Some non-acid monomers may also be included, usually in minor amounts, in preparing the absorbent polymers. Such non-acid monomers include, for example, monomers containing the following types of functional groups: carboxylate or sulfonate esters, hydroxyl groups, amide groups, amino groups, nitrile groups, quaternary ammonium salt groups, and aryl groups (e.g. phenyl groups, such as those derived from styrene monomer). Other potential non-acid monomers include unsaturated hydrocarbons such as ethylene, propylene, 1-butene, butadiene, or isoprene.

In some embodiments, the binder or expandable phase comprises substances which are capable of becoming freely permeable following hydration in aqueous fluids. Such substances include polysaccharides, such as gelatin, saccharose, sorbitol, mannanes, jaluronic acid, polyaminoacids, polyalcohols, polyglycols, or the like. In addition to the foregoing, the swellable polymer may also include additional excipients such as lubricants, flow promoting agents, plasticizers, and anti-sticking agents. For example, the binder or expandable phase may further include polyethylene glycol, polyvinylpyrrolidone, talc, magnesium stearate, glyceryl behenate, stearic acid, or titanium dioxide.

In various embodiments, the particle size distribution of the binder or expandable phase material may be about 10 micrometers, 13 micrometers, 85 micrometers, 100 micrometers, 151 micrometers, 200 micrometers and all subranges therebetween. In some embodiments, at least 75% of the particles have a size from about 10 micrometers to about 200 micrometers. In some embodiments, at least 85% of the particles have a size from about 10 micrometers to about 200 micrometers. In some embodiments, at least 95% of the particles have a size from about 10 micrometers to about 200 micrometers. In some embodiments, all of the particles have a size from about 10 micrometers to about 200 micrometers. In some embodiments, at least 75% of the particles have a size from about 20 micrometers to about 180 micrometers. In some embodiments, at least 85% of the particles have a size from about 20 micrometers to about 180 micrometers. In some embodiments, at least 95% of the particles have a size from about 20 micrometers to about 180 micrometers. In some embodiments, all of the particles have a size from about 20 micrometers to about 180 micrometers.

Cryopreservation and Lyophilization

After decellularization, the tissue can be frozen (e.g., cryopreserved) and in other cases, freeze-dried or lyophilized. Before freezing, the tissue can be incubated in a cryopreservation solution. This solution generally contains one or more cryoprotectants to minimize ice crystal damage to the structural ATM that could occur during freezing.

Examples of useful cryoprotectants include without limitation dimethylsulfoxide (DMSO), dextran, sucrose, 1,2-propanediol, glycerol, sorbitol, fructose, trehalose, raffinose, propylene glycol, 2, 3 butane diol, hydroxyethyl starch, polyvinylpyrrolidone (PVP), proline (or other protein stabilizers), human serum albumin or combinations thereof. If the tissue is to be freeze-dried, the solution will generally also contain one or more dry-protective components, to minimize structural damage during drying and may include a combination of an organic solvent and water which undergoes neither expansion or contraction during freezing. The cryoprotective and dry-protective agents can be the same, or one or more substances. If the tissue is not going to be freeze-dried, it can be frozen by placing it (in a sterilized container) in a freezer at about −80° C., or by plunging it into sterile liquid nitrogen, and then storing at a temperature below −160° C. until use.

Any suitable freeze-drying suspension medium may be employed. For example, the freeze-drying suspension medium may comprise water or an aqueous medium, such as saline. In some embodiments, the use of freeze-drying suspension media containing collagen-swelling levels of acids or alkalis, may be included. In other embodiments, the use of freeze-drying suspension media containing collagen-swelling levels of acids or alkalis, may be excluded in order to avoid damage to the fiber architecture and molecular ultrastructure of the collagen particles. By way of example, freeze-drying suspension media having a pH within the range of about 5 to 12 may be used to suspend crosslinked acellular collagen particles, whereas for non-crosslinked acellular collagen particles the freeze-drying suspension media may have a pH within the range of about 6 to 8.

The acellular collagen particles may be suspended in the freeze-drying suspension medium at a range of different concentrations. In various embodiments, the concentration of acellular collagen particles suspended in the freeze-drying suspension medium is in the range of 10 to 80% (w/v), although other concentrations may be used. At the higher end of this range, the suspension of acellular collagen particles in the freeze-drying medium has a relatively thick, pasty consistency.

The process may optionally include a step of mixing the suspension of acellular collagen particles in the freeze-drying suspension medium. This ensures even distribution of the acellular collagen particles in the freeze-drying suspension medium. Harsh mechanical mixing treatments such as homogenization or blending should be avoided, however, in order to minimize acellular collagen damage.

The suspension of acellular collagen particles may, for example, be molded, formed or cast into the desired shape prior to freeze-drying. In many implementations, the freeze-drying suspension medium and acellular collagen particles suspended therein are held in a suitable mold during the freeze-drying step. The process can therefore be used for the manufacture of acellular collagenous materials of predetermined shapes, which can readily be varied by using different molds. Examples of suitable shapes include sheets, plugs, blocks, wedges, beads, ropes, or variations thereof.

If the ATM is to be frozen and freeze-dried, following incubation in the cryopreservation solution, the tissue can be packaged inside a sterile vessel that is permeable to water vapor yet impermeable to bacteria, e.g., a water vapor permeable pouch or glass vial. One side of a useful pouch consists of medical grade porous TYVEK® membrane, a trademarked product of DuPont Company of Wilmington, Del. This membrane is porous to water vapor and impervious to bacteria and dust. The TYVEK® membrane is heat sealed to an impermeable polythylene laminate sheet, leaving one side open, thus forming a two-sided pouch. The open pouch is sterilized by irradiation (e.g., γ-irradiation) prior to use. The tissue is aseptically placed (through the open side) into the sterile pouch. The open side is then aseptically heat sealed to close the pouch. The packaged tissue is henceforth protected from microbial contamination throughout subsequent processing steps.

In various embodiments, crosslinking may be carried out to impart additional physical strength to the acellular collagenous material, and an increased resistance to digestive enzymes that may be present in a wound healing environment. Surprisingly, freeze-dried acellular collagenous material formed from particles of crosslinked acellular collagen has been found to have improved flexibility as compared to corresponding acellular collagenous material formed from non-crosslinked acellular collagen particles. This is beneficial for use of the acellular collagenous material in wound care. Thus, in various embodiments, the acellular collagen particles are crosslinked.

In various embodiments, crosslinking agents include polyisocyanates, in some cases, diisocyanates. The polyfunctional isocyanates react with amino or hydroxyl groups of different protein chains forming a material which has a stable structure, while retaining the original architecture of the acellular collagen and which is resistant to enzymatic attack. It is known that antigenicity is associated with the amino groups of the protein chains of acellular collagen, and reacting the amino groups with isocyanate removes any antigenicity associated with these groups. In certain aspects, diisocyantes include aliphatic, aromatic and alicyclic diisocyanates as exemplified by 1,6-hexamethylene diisocyanate, toluene diisocyanate, 4,4'-diphenylmethane diisocyanate, and 4,4'-dicyclohexylmethane diisocyanate, respectively. In other aspects, a useful diisocyanate is hexamethylene diisocyanate (HMDI). Carbodiimide crosslinking agents may also be used, such as 1-ethyl-3-[3-dimethylaminopropyl]carbodiimide hydrochloride (EDC).

The extent of crosslinking of the acellular collagen particles may be varied. Usefully, this provides a mechanism for controlling the rate at which the acellular collagenous material is resorbed or degraded during use. The resistance to degradation tends to increase as the extent of crosslinking is increased.

By way of example, crosslinking of the acellular collagen particles may be carried out using HMDI. In certain embodiments, the HMDI may be used at a concentration of around 0.01 g to 0.5 g per 50 g of acellular collagen. If the concentration is too high, this may result in over-crosslinking and foreign body reactions. Crosslinking may be carried out at a range of different time periods. By way of example, the acellular collagen may be exposed to the crosslinking agent for between around 1 hour to around 3 days. Typically, crosslinking is carried out for at least 12 hours, in some cases, at least 20 hours. It will be appreciated that the crosslinking conditions may routinely be varied in order to adjust the extent of crosslinking.

In some embodiments, a lyophilized implant comprises a sterol, for example, an effective amount of Oxy133. A slurry containing an acellular porcine collagen, bone material and the oxysterol is freeze-dried or lyophilized. Any suitable liquid can be used in the slurry to mix the acellular porcine collagen, bone material and an oxysterol together to form the slurry. Suitable liquids include, for example, aqueous preparations such as water, saline solution (e.g. physiological saline), sugar solutions, or combinations thereof.

More particularly, lyophilized implant formulations are typically first prepared as slurries, then placed into trays, frozen and lyophilized. The total liquid volume required for pre-lyophilization can be equal to, or more than the amount of liquid required for post lyophilization.

The lyophilization process typically includes sublimation of water from a frozen implant formulation under controlled conditions. Lyophilization can be carried out using standard equipment as used for lyophilization or vacuum drying. The cycle may be varied depending upon the equipment and facilities used for the fill and finish.

Initially, in some embodiments, a slurry containing the implant components including Oxy133 is placed into molds of desired shapes in a lyophilization chamber under a range of temperatures and then subjected to temperatures well below the slurry's freezing point, generally for several hours. In many cases, the temperature can be at or below about –40° C. for at least 2 hours. After freezing is complete, the lyophilization chamber and the condenser are evacuated through vacuum pumps, the condenser surface having been previously chilled by circulating refrigerant. The condenser would have been chilled below the freezing point of the slurry to about –40°, in some cases to about –50° C. or lower, in other cases, to about –60° C. or lower. Additionally, evacuation of the chamber should continue until a pressure of about 50 mTorr to about 600 mTorr, in some cases, about 50 to about 150 mTorr is obtained.

The lyophilized implant is then warmed under vacuum in the chamber and condenser. This usually would be carried out by warming the shelves within the lyophilizer on which the molds containing the lyophilized implant rest during the lyophilization process at a pressure ranging from about 50 mTorr to about 600 mTorr. The warming process would optimally take place very gradually, over the course of several hours. For example, the temperature should initially be increased from about –30° C. to about –10° C. and maintained for about 10-70 hours. Additionally, the lyophilized implant can be increased from the freezing temperature to about 25° C. to –40° C. over a period of 30-192 hours. Complete drying can be accomplished by stabilization of vacuum, condenser temperature and lyophilized implant shelf temperature. After the initial drying, the temperature of the lyophilized implant can be increased to about 25° C. to –40° C. and maintained for about 5-40 hours. Once the drying cycle is completed, the pressure in the chamber can be slowly released to atmospheric pressure (or slightly below) with sterile, dry-nitrogen gas (or equivalent gas).

In some embodiments, after lyophilization, the implant is from about 95 to about 99.5% free of moisture. In various embodiments, the implant is about 95, 95.5, 96, 96.5, 97, 97.5, 98, 98.5, 99, or about 99.5% free of moisture. In some embodiments, the implant has about 0.5% to about 5% moisture content remaining after lyophilization. In various embodiments, the implant has about 0.5, 1, 1.5, 2, 2.5, 3, 3.5, 4, 4.5, or 5% moisture content remaining after lyophilization. Lyophilized implants are stable and can be stored at a wide range of temperatures. Lyophilized implants can be stored at or below 30° C., for example, refrigerated at 4° C., or at room temperature (e.g., approximately 25° C.).

The lyophilized implant is a stable implant that is a convenient way to make a moldable implant after reconstitution and implant it at or near a bone defect. Lyophilized implants of Oxy133 are typically reconstituted for use by addition of an aqueous solution to rehydrate the lyophilized implant. A wide variety of aqueous solutions can be used to reconstitute a lyophilized implant, for example, physiologically acceptable water, physiological saline, sodium chloride, dextrose, Lactated Ringer's solution, phosphate buffered saline (PBS), blood, bone marrow aspirate, bone marrow fractions or a combination thereof.

Method of Making

In some embodiments, the implant is made by adding an oxysterol in an amount of from about 20 wt. % to about 90 wt. % to the ATM or an acellular porcine collagen, the acellular porcine collagen being in an amount of about 0.1 wt. % to about 20 wt. % based on the total weight of the implant to form a mixture. In other embodiments, porous ceramic particles are added to the mixture to form the implant, the porous ceramic particles being in an amount of about 30 wt. % to about 99.5 wt. % based on a total weight of the implant. In some embodiments, the mixture forms a slurry, a putty, or paste, which can be lyophilized.

In some embodiments, in manufacturing the implant, a mixture of the ATM material (e.g., acellular collagen and oxysterol) is combined with the bone material and a liquid to wet the material to form a slurry, a putty, or paste in about 30 seconds. Any suitable liquid can be used including, for example, aqueous preparations such as water, saline solution (e.g. physiological saline), sugar solutions, protic organic solvents, or liquid polyhydroxy compounds such as glycerol and glycerol esters, or mixtures thereof. The liquid may, for example, constitute about 5 to about 70 weight percent of the mixed composition prior to lyophilization. Once wetted, the implant becomes moldable or flowable in slurry form and then, in some cases, may be lyophilized.

In one embodiment of manufacture, an acelluar collagen mixture can be combined with Permacol® paste, an oxysterol (e.g., Oxy133) and a liquid, desirably with an aqueous preparation, to form a moldable cohesive mass. Excess liquid can be removed by any suitable means, including for example by applying the cohesive mass to a liquid-permeable mold or form and draining away excess liquid.

In some embodiments, the implant is formed by mixing the Permacol® paste, acellular collagen and the oxysterol until a coherent mass is formed. In other aspects, the bone materials, Permacol® paste and the oxysterol are wetted and mixed in a mixing syringe or similar device.

In some embodiments, the mixture of the ATM, bone materials and/or oxysterol are molded to take the form of the implant. Before, during or after molding, including in some instances the application of compressive force to the ATM, the acellular porcine collagen can be subjected to one or more additional operations such as heating, lyophilizing and/or crosslinking.

Crosslinking can be used to improve the strength of the formed ATM. Alternatively, the surface of the ATM can be crosslinked to reduce the size of the pores of the porous interior and thereby form the exterior of the ATM that is less permeable and/or less porous than a porous interior. Crosslinking can be achieved, for example, by chemical reaction, the application of energy such as radiant energy (e.g., UV light or microwave energy), drying and/or heating and dye-mediated photo-oxidation, dehydrothermal treatment, enzymatic treatment or others.

In some embodiments, a chemical crosslinking agent is used. Examples of suitable crosslinking agents include those that contain bifunctional or multifunctional reactive groups, and which react with the ATM. Chemical crosslinking can be introduced by exposing the ATM material to a chemical crosslinking agent, either by contacting it with a solution of the chemical crosslinking agent or by exposure to the vapors of the chemical crosslinking agent. This contacting or exposure can occur before, during or after a molding operation. In any event, the resulting material can then be washed to remove substantially all remaining amounts of the chemical crosslinker if needed or desired for the performance or acceptability of the final implantable ATM.

Suitable chemical crosslinking agents include mono- and dialdehydes, including glutaraldehyde and formaldehyde; polyepoxy compounds such as glycerol polyglycidyl ethers, polyethylene glycol diglycidyl ethers and other polyepoxy and diepoxy glycidyl ethers; tanning agents including polyvalent metallic oxides such as titanium dioxide, chromium dioxide, aluminum dioxide, zirconium salt, as well as organic tannins and other phenolic oxides derived from plants; chemicals for esterification or carboxyl groups followed by reaction with hydrazide to form activated acyl azide functionalities in the collagen; dicyclohexyl carbodiimide and its derivatives as well as other heterobifunctional crosslinking agents; hexamethylene diisocyante (HMID); and/or sugars, including glucose, will also crosslink the ATM material.

In some embodiments, the matrices are formed by mixing the oxysterol with a polymer slurry such as acellular collagen and pouring the mixture into a shaped mold. The composite mixture is freeze dried and possibly chemically crosslinked and cut to the final desired shape, in some cases, into strips.

In some embodiments, the oxysterol is solubilized and mixed with the acellular porcine collagen present in the Permacol® paste. In some embodiments, the oxysterol is solubilized in an organic solvent (e.g., ethanol) or optionally with a co-solvent (e.g., PEG). Suitable examples of organic solvents include tetrahydrofuran, diethyl ether, dichloromethane, ethyl acetate, acetone, n,n-dimethylformamide, acetonitrile, dimethyl sulfoxide, ammonia, t-butanol, n-propanol, ethanol, methanol, acetic acid or combinations thereof. In some embodiments, the oxysterol may be mixed in a 25:75 to a 75:25 ratio with the solvent. In some embodiments, the oxysterol is mixed in a 50:50 ratio with the solvent to form a solution or suspension of the oxysterol, which can then be added to the Permacol® paste and/or the bone materials.

For example, if the oxysterol is Oxy133, it is typically only slightly soluble or insoluble in water. The Oxy133 can be solubilized in a non-aqueous solvent, such as for example, ethanol and mixed into a solution or suspension. In some embodiments, the Oxy133 can be filtered by passing the Oxy133 and solvent through a filter (e.g., 0.22 microns). This will remove bacteria and other larger-size particulates out of the composition. The Oxy133 used in the composition can be micronized before it is mixed with solvents and other excipients. In various embodiments, the particle size of the Oxy133 can range from about 1 micron to 250 microns. In some embodiments, the Oxy133 can have a particle size of from about 5 microns to about 100 microns or from about 20 to 50 microns. The Oxy133 in the solution or suspension can be added to a slurry of acellular porcine collagen and/or the ceramic particles, mixed, and then dried.

The implant may be used to repair bone and/or cartilage at a target tissue site, e.g., one resulting from injury, defect brought about during the course of surgery, infection, malignancy or developmental malformation. The implant can be utilized in a wide variety of orthopedic, periodontal, neurosurgical, oral and maxillofacial surgical procedures such as the repair of simple and/or compound fractures and/or non-unions; external and/or internal fixations; joint reconstructions such as arthrodesis; general arthroplasty; cup arthroplasty of the hip; femoral and humeral head replacement; femoral head surface replacement and/or total joint replacement; repairs of the vertebral column including spinal fusion and internal fixation; tumor surgery, e.g., deficit filling; discectomy; laminectomy; excision of spinal cord tumors; anterior cervical and thoracic operations; repairs of spinal injuries; scoliosis, lordosis and kyphosis treatments; intermaxillary fixation of fractures; mentoplasty; temporomandibular joint replacement; alveolar ridge augmentation and reconstruction; inlay implantable matrices; implant placement and revision; sinus lifts; and/or cosmetic procedures. Specific bones which can be repaired or replaced with the implantable ATM herein include the ethmoid, frontal, nasal, occipital, parietal, temporal, mandible, maxilla, zygomatic, cervical vertebra, thoracic vertebra, lumbar vertebra, sacrum, rib, sternum, clavicle, scapula, humerus, radius, ulna, carpal bones, metacarpal bones, phalanges, ilium, ischium, pubis, femur, tibia, fibula, patella, calcaneus, tarsal and/or metatarsal bones.

Application of the Oxysterol to the ATM

In some embodiments, a therapeutic agent (e.g., oxysterol, with or without one or more growth factors) may be disposed on or in the implant by hand, mixing, spraying, impregnating, injecting, brushing and/or pouring to infuse the implant.

Application of the oxysterol to the implant may occur at the time of surgery, by the manufacturer or in any other suitable manner. For example, the oxysterol uniformly dispersed within the Permacol® paste may be placed in a syringe for delivery to a surgery site. In other aspects, a lyophilized mixture of Permacol® and the oxysterol may be reconstituted using a syringe and the syringe can be placed into an interior of the implant via insertion of a needle or cannula (piercing the ATM) and injecting the oxysterol so it is evenly distributed throughout the porous interior of the ATM.

In some embodiments, the oxysterol may be applied to the ATM prior to combining the materials and forming it into the final implant shape. Indeed, the oxysterol can be blended into the natural or synthetic polymer (e.g., acellular collagen, in some aspects, crosslinked) and poured into molds of the final shape of the implant. Alternatively, the oxysterol, such as Oxy133, may be applied onto and/or into the porous loaded ATM after forming it into the final shape by mixing, soaking, dripping, injecting, spraying, or a combination thereof.

The growth factors and the oxysterol of the present application may be disposed on or in the ATM with other therapeutic agents. For example, the growth factor may be disposed on or in the carrier by electrospraying, ionization spraying or impregnating, vibratory dispersion (including sonication), nozzle spraying, compressed-air-assisted spraying, brushing and/or pouring.

In some embodiments, the interior of the implant is loaded with oxysterol that functions as an osteoinductive factor. In other aspects, the oxysterol can be disposed in a vial and then a surgeon can mix a fluid with the oxysterol, which can be used to load the Permacol® paste prior to application to a bone defect site.

The amount of oxysterol, may be sufficient to cause bone and/or cartilage growth. In some embodiments, the oxysterol is Oxy133 and is contained in one or more ATMs in an amount of from 1 to 2 mg per cubic centimeter of the ATM.

In some embodiments, the oxysterol is supplied in a liquid carrier (e.g., an aqueous buffered solution or organic solvent). Exemplary aqueous buffered solutions include, but are not limited to, TE, HEPES (2-[4-(2-hydroxyethyl)-1-piperazinyl]ethanesulfonic acid), MES (2-morpholinoethanesulfonic acid), sodium acetate buffer, sodium citrate buffer, sodium phosphate buffer, a Tris buffer (e.g., Tris-HCL), phosphate buffered saline (PBS), sodium phosphate, potassium phosphate, sodium chloride, potassium chloride, glycerol, calcium chloride or a combination thereof. In various embodiments, the buffer concentration can be from about 1 mM to 100 mM. In some embodiments, the oxysterol is provided in a vehicle (including a buffer) containing sucrose, glycine, L-glutamic acid, sodium chloride, and/or polysorbate 80. Exemplary organic solvents or non-aqueous solvents include DMSO, acetic acid, acetone, DME, DMF, MTBE, acetonitrile, butanol, butanone, t-butyl alcohol, ethanol, polyethylene glycol, methanol, chlorobenzene, chloroform, toluene, propanol, pentane, heptane, ethanol, diethyl ether, or the like.

In some embodiments, the oxysterol disposed in the acellular tissue matrix is OXY133 and comprises polymorphic Form A that produces an X-ray powder diffraction pattern comprising one or more of the following reflections: 6.1, 12.3, 16.4, 17.91, 18.6 and 20.94±0.2 degree 2θ before it is put in the matrix, or Form B that produces an X-ray powder diffraction pattern comprising one or more of the following reflections: 5.9, 11.9, 13.3, 16.1, 17.96, and 18.82±0.2 degree 2θ before it is put in the matrix; or a mixture thereof.

Method of Treating

In some embodiments, the implant comprises an acellular porcine collagen, in some cases, a crosslinked acellular porcine collagen and an oxysterol, such as, for example, Oxy133 monohydrate, to promote osteogenesis. In other embodiments, the implant can also include bone material and a fluid. In use, Oxy133 provides therapeutic treatment for bone conditions. Oxy133 facilitates bone formation, osteoblastic differentiation, osteomorphogenesis and/or osteoproliferation. The implant can be administered to treat open fractures and fractures at high risk of non-union, and in subjects with spinal disorders. That is, Oxy133 can induce spinal fusion and may help treat degenerative disc disease or arthritis affecting the lumbar or cervical vertebrae.

In some embodiments, the implant, after it is lyophilized, is administered by wetting it to impart malleability and moldability properties to the implant. The implant can be molded to different sizes, shapes and configurations. In various embodiments, the moldable implant comprising an ATM and an oxysterol, can be placed into a syringe so that a surgeon can deliver it to a surgical site, and/or the syringe containing the implant is further placed into a vacuum pouch for further preservation prior to use. In other cases, the implant is lyophilized and then placed into a vacuum sealed pouch for preservation prior to hydration and use by a surgeon to treat a bone defect. Whether in a syringe or vacuum packed, these implants can be stored at about 40° C. and 75% ambient humidity.

There are several factors that can be taken into consideration in determining the size, shape and configuration of the implant. For example, both the size and shape may allow for ease in positioning the implant at the target tissue site that is selected. In addition, the shape and size of the implant should be selected so as to minimize or prevent the implant from moving after implantation. In various embodiments, the implant can be shaped like a rod or a flat surface such as a film or sheet (e.g., ribbon-like) or the like. Flexibility may be a consideration so as to facilitate placement of the device.

Mesenchymal stem cells treated with Oxy133 have increased osteoblast differentiation. Thus, in some embodiments, an ATM comprising Oxy133 may be implanted into a spinal site with mesenchymal stem cells to induce bone growth through osteoblast differentiation. Periosteum tissue is one tissue type that is involved early during a normal bone fracture repair process and can recruit various cell types (e.g., mesenchymal stem cells) and bone growth factors necessary for bone fracture repair. Thus, in some embodiments, periosteum tissue is utilized as a source of mesenchymal stem cells and/or growth factors in a demineralized bone composition.

In some embodiments, an implant comprising Oxy133 may be implanted or injected directly into a surgical site in a patient. In some embodiments, the implant is configured to release Oxy133 in the form of a depot. In some embodiments, a plurality of matrices is provided (e.g., in a kit) and administered to a surgical site that triangulate and/or surround the site needed for bone growth. In various embodiments, a plurality of matrices comprises about 1, 2, 3, 4, 5, 6, 7, 8, 9 or 10 matrices. In some embodiments, a plasticizer is used to lower glass transition temperature in order to affect stability of the implant.

Radiographic markers can be included on the implant to permit the user to position it accurately into the target site of the patient. These radiographic markers will also permit the user to track movement and degradation of the implant at the site over time. In this embodiment, the user may accurately position the implant in the site using any of the numerous diagnostic imaging procedures. Such diagnostic imaging procedures include, for example, X-ray imaging or fluoroscopy. Examples of such radiographic markers include, but are not limited to, ceramics, barium, phosphate, bismuth, iodine, tantalum, tungsten, and/or metal beads or particles. In various embodiments, the radiographic marker could be a spherical shape or a ring around the implant. The ceramic in the composition can also be used as a radiographic marker.

In some embodiments, the implant comprising the oxysterol uniformly disposed in an ATM can be administered to the target site by being shaped according to the needs of a medical procedure and passed through a "cannula" or "needle" that can be a part of a delivery device e.g., a syringe, a gun delivery device, or any medical device suitable for the delivery of the implant to a targeted organ or anatomic region. The cannula or needle of the device is designed to cause minimal physical and psychological trauma to the patient.

Sterilization

The acellular porcine collagen, bone material, oxysterol and devices to administer the implant may be sterilizable. In various embodiments, one or more components of the ATM, and/or medical device used to administer the matrix may be sterilizable by radiation in a terminal sterilization step in the final packaging. Terminal sterilization of a product provides greater assurance of sterility than from processes such as an aseptic process, which require individual product components to be sterilized separately and the final package assembled in a sterile environment.

Typically, in various embodiments, gamma radiation is used in the terminal sterilization step, which involves utilizing ionizing energy from gamma rays that penetrates deeply into the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In some embodiments, the implant may be packaged in a moisture resistant package and then terminally sterilized by gamma irradiation. In use, the surgeon removes one or all components from the sterile package for use.

In various embodiments, electron beam (e-beam) radiation may be used to sterilize one or more components of the ATM. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity.

Other methods may also be used to sterilize the implantable ATM and/or one or more components of the ATM, including, but not limited to, gas sterilization, such as, for example, with ethylene oxide or steam sterilization.

Kits

In various embodiments, a kit is provided comprising the oxysterol (e.g., Oxy133), ATM (e.g. Permacol® paste), bone material, and/or diluents. The kit may include additional parts along with the implantable ATM combined together to be used to implant the ATM (e.g., wipes, needles, syringes, mixing syringe or other mixing device). In some instances, the oxysterol has been already incorporated into the ATM present in the kit. The kit may include the ATM with or without an oxysterol in a first compartment. The second compartment may include a vial holding the diluent and any other instruments needed for the localized delivery. A third compartment may include gloves, drapes, wound dressings and other procedural supplies for maintaining sterility of the implanting process, as well as an instruction booklet, which may include a chart that shows how to implant the ATM after hydrating it. A fourth compartment may include additional needles and/or sutures. Each tool may be separately packaged in a plastic pouch that is radiation sterilized. A fifth compartment may include an agent for radiographic imaging. A cover of the kit may include illustrations of the implanting procedure and a clear plastic cover may be placed over the compartments to maintain sterility.

These and other aspects of the present application will be further appreciated upon consideration of the following Examples, which are intended to illustrate certain particular embodiments of the application but are not intended to limit its scope, as defined by the claims.

EXAMPLES

Permacol® paste, an acellular collagen paste derived from porcine dermis contains 20% acellular crosslinked collagen and 80% saline solution. The collagen component is decellularized porcine dermis that is cryogenically milled and then crosslinked using hexamethylene diisocyanate (HMDI). Moldable implant formulations containing Oxy133 mixed with Permacol® paste were prepared and utilized in spinal fusion studies conducted in rabbits and rats. These compositions were neither lyophilized nor loaded into a syringe. These compositions were delivered by implanting them onto the decorticated transverse processes of the studied rabbits and rats.

Example 1

In this example, Permacol® paste was mixed with Oxy133 monohydrate in various amounts as listed in Table 1, below. Moldable formulations of Permacol® paste and Oxy133 monohydrate were applied in various amounts to rabbits single level posterolateral lumber spine fusions.

Moldable formulations of crosslinked bovine collagen were also applied in the same amounts to rabbits in single level posterolateral lumbar spine fusions. Fusion rates were determined by manual palpation of the operated spine segments. The results are summarized in Table 1, below.

TABLE 1

Rabbit Single Level Posterolateral Fusion Study

| Oxy Dose (mg Oxy133/ cc implant) | Moldable Formulation-Permacol ® Paste Fusion Rate (%) | Moldable Formulation-Crosslinked Bovine Collagen Fusion Rate (%) |
|---|---|---|
| 10 | 50 | 20 |
| 40 | 66.7 | 50 |
| 80 | 100 | 33.3 |
| 160 | 75 | 33.3 |
| 240 | 66.6 | 33.3 |

From the fusion rates listed in Table 1, above, it is evident that the moldable formulation of Permacol® paste and 80 mg/cc of Oxy133 monohydrate provided the highest fusion rate of 100% when implanted into rabbits subjected to single level posterolateral lumbar spine fusion, which was an unexpected result. Fusion rates achieved by applying crosslinked bovine collagen-based implants to rabbits in identical procedures were significantly lower.

Example 2

In this example, Permacol® paste was mixed with Oxy133 monohydrate in various amounts as listed in Table 2, below. Moldable formulations of Permacol® paste and Oxy133 monohydrate were applied in various amounts to rats during two-level posterolateral lumber spine fusions. Moldable formulations with crosslinked bovine collagen were also applied in the same amounts to rats during two-level posterolateral lumbar spine fusions. Fusion rates were determined by manual palpation of the operated spine segments. The results are summarized in Table 2.

TABLE 2

Rat 2-Level Posterolateral Fusion Study

| Oxy Dose (mg Oxy133/ cc implant) | Moldable Formulation-Permacol ® Paste Fusion Rate (%) | Moldable Formulation-Crosslinked Bovine Collagen Fusion Rate (%) |
|---|---|---|
| 0 | 0 | 0 |
| 5 | 0 | 10 |
| 10 | 60 | 80 |
| 20 | 90 | 90 |
| 40 | 100 | 90 |
| 80 | 100 | 90 |

Figure 2:
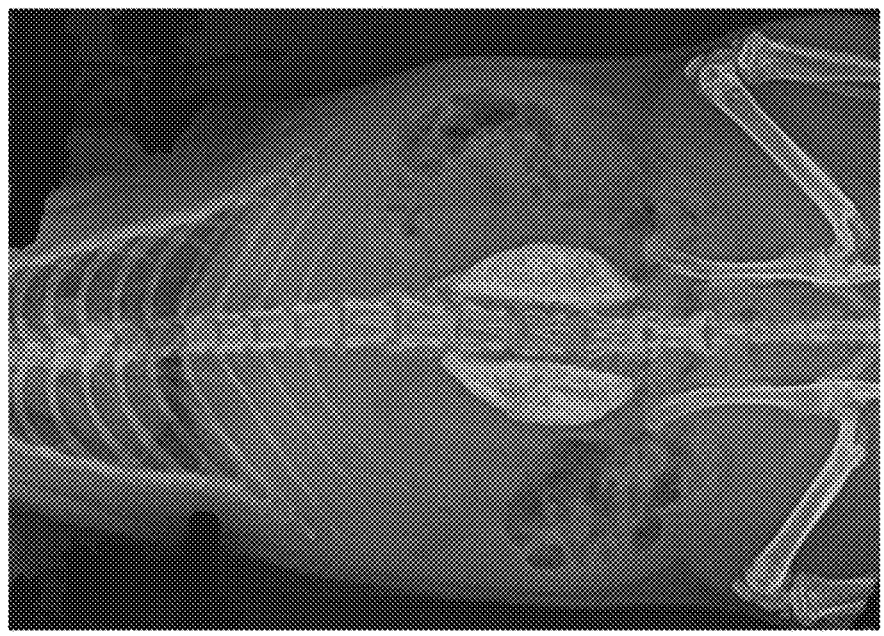
FIG. 2 illustrates an X-ray radiograph taken of the same rat 4 weeks post-operatively after undergoing a two-level posterolateral lumbar spine fusion where the implant was a malleable paste containing Permacol®, Oxy133 monohydrate, ceramic and carboxymethylcellulose.
Figure 3:
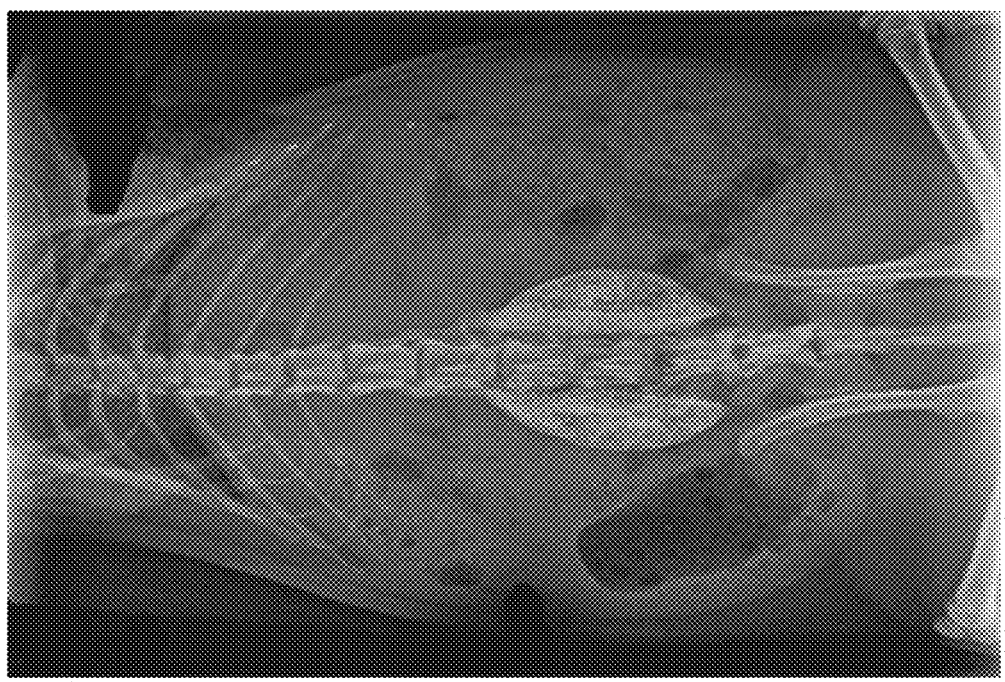
FIG. 3 illustrates an X-ray radiograph taken of the same rat 8 weeks post-operatively after undergoing a two-level posterolateral lumbar spine fusion where the implant was a malleable paste containing Permacol®, Oxy133 monohydrate, ceramic and carboxymethylcellulose.

From the fusion rates listed in Table 2, above, it is evident that moldable formulations of Permacol® paste and both 40 mg/cc and 80 mg/cc of Oxy133 monohydrate, respectively, provided the highest fusion rate of 100% when injected into rats during two-level posterolateral lumbar spine fusions (PLF). Fusion rates achieved by implants containing crosslinked bovine collagen for the same fusion procedures are significantly lower. These unexpected results were confirmed by X-ray radiographs taken of a rat immediately post-operative undergoing a two-level posterolateral lumbar spine fusion procedure as illustrated in FIG. 1 and post-operatively at 4 week and 8 week intervals as illustrated in FIGS. 2 and 3, respectively. FIGS. 1, 2 and 3 represent results taken of a two-level posterolateral fusion procedure conducted on a rat that received a bilateral 0.5 cc implant of a moldable paste of Permacol® mixed with 40 mg/l cc of Oxy133 monohydrate, ceramic granules and sodium carboxymethylcellulose (CMC) spanning the L3 to L5 transverse processes of the rat. In particular, the composition of the moldable paste implant utilized in this procedure is summarized in Table 3, below.

TABLE 3

Composition of Moldable Implant

| Description | Permacol ® Paste (mg) | Ceramic (mg) | CMC (mg) | Oxy133 (mg) |
|---|---|---|---|---|
| 40 mg/cc Oxy133 | 750 | 750 | 20 | 40 |

By comparison to the immediate post-operative X-ray radiograph of FIG. 1, FIGS. 2 and 3 illustrate new bone formation along the lateral margins and trabecular bones in the interior of the implants. Remodeling of the implant material was evident in FIGS. 2 and 3 by comparison to FIG. 1, the post-operative radiograph. The presence of bone bridging between the L3-L5 transverse processes evidences that the rat was determined to be radiographically fused.

Figure 4:
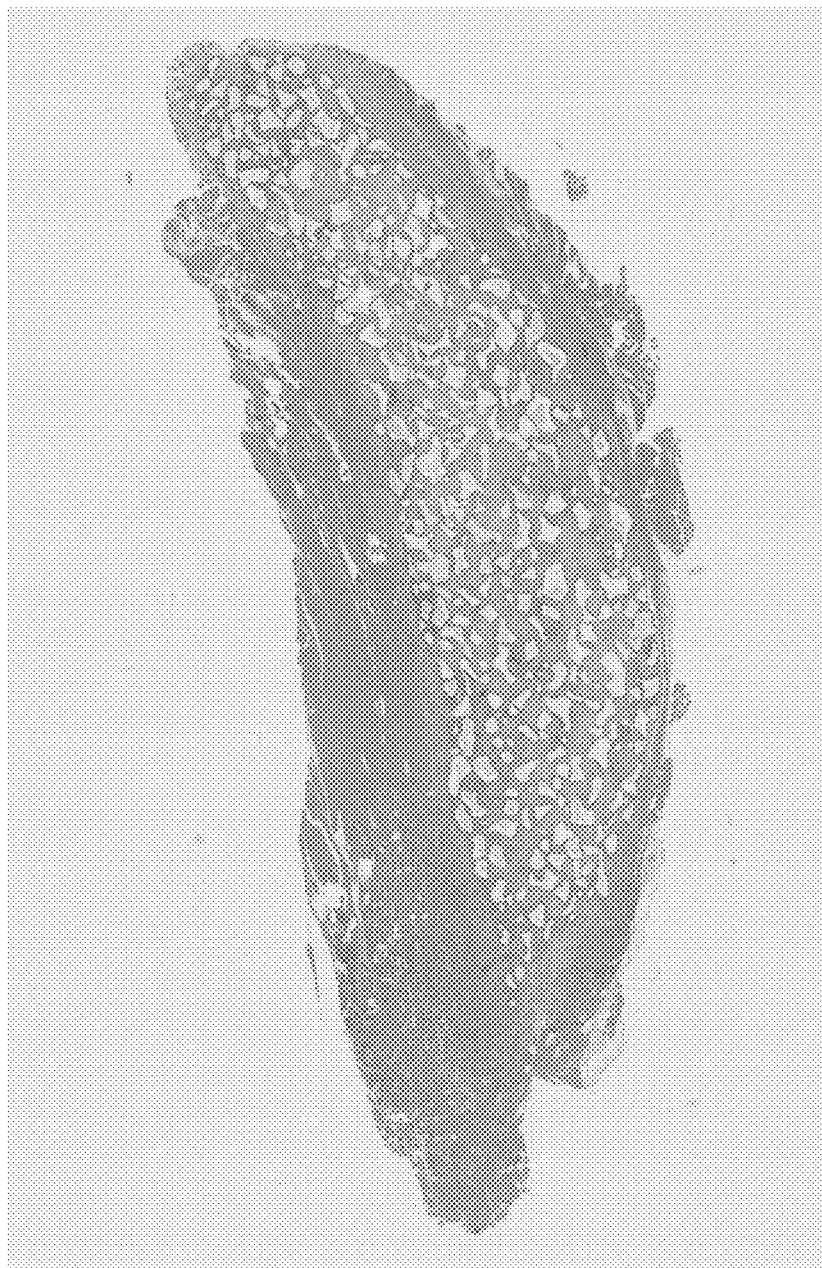
FIG. 4 illustrates a histology slide of a control group rat that had been implanted with an implant material that did not contain any oxysterol including Oxy133 monohydrate.
Figure 5:
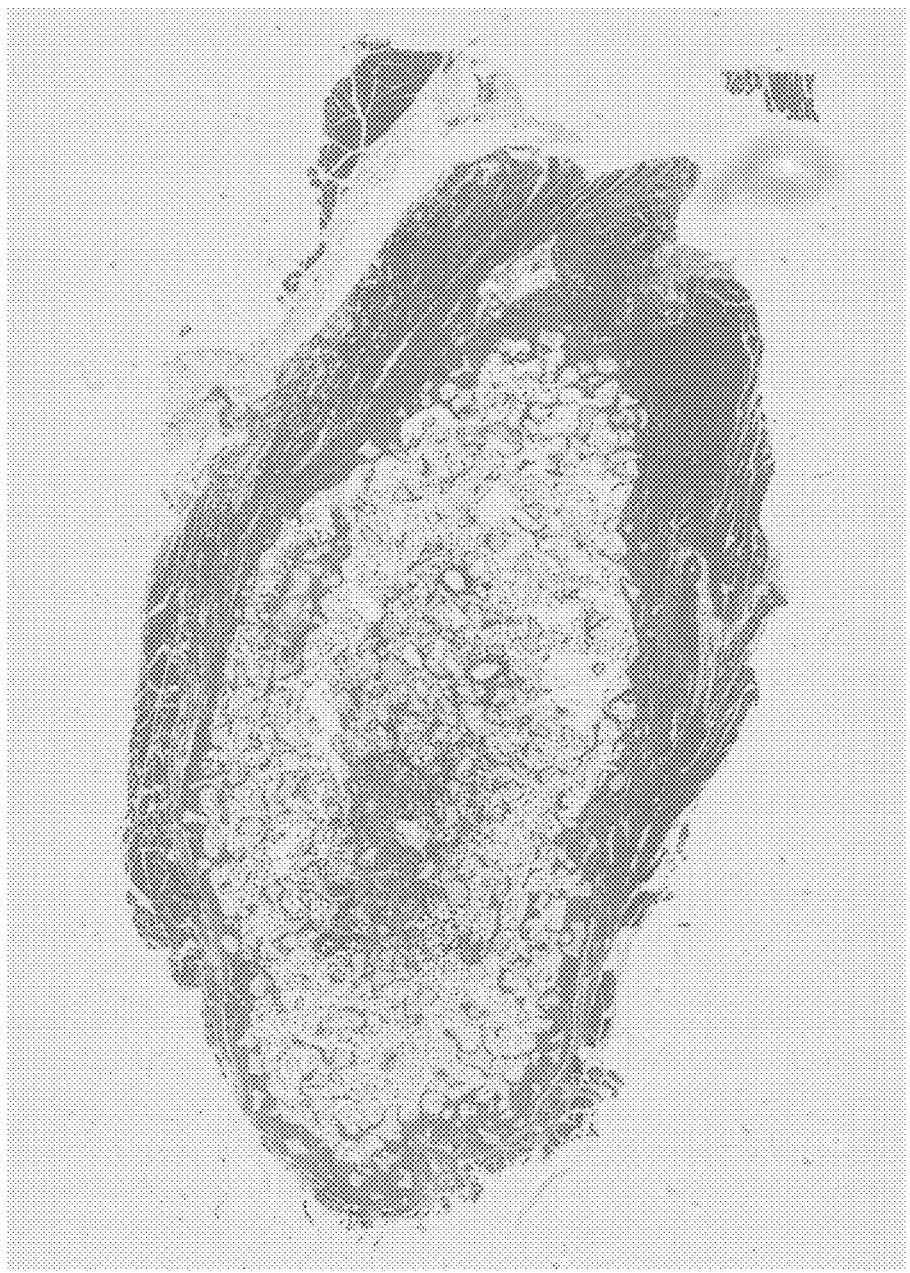
FIG. 5 illustrates a histology slide (e.g., H&E stain) of the same rat that underwent two-level posterolateral lumbar spine fusion at 8 weeks after the procedure where the implant was a malleable paste containing Permacol®, Oxy133 monohydrate, ceramic and carboxymethylcellulose.
Figure 6:
FIG. 6 illustrates a histology slide (e.g., H&E stain) of the same rat that underwent two-level posterolateral lumbar spine fusion at 8 weeks after the procedure where the implant was a malleable paste containing Permacol®, Oxy133 monohydrate, ceramic and carboxymethylcellulose.

FIGS. 4, 5 and 6 are histology slides from rats that underwent two-level posterior lateral fusions. The histology slide of FIG. 4 is the image of a control group rat that was a carrier only of the implant material without Oxy133. In this image, there is no new bone formation and fibrous tissue is seen between the residual ceramic granules. FIGS. 5 and 6 are histology slides of the rat that underwent two-level posterior lateral fusion containing a moldable implant formulation as in Table 3 above and of which X-ray radiographs after 4 and 8 weeks, respectively, were taken as illustrated in FIGS. 2 and 3. FIGS. 5 and 6 clearly show the disappearance of ceramic granules and an increase presence of adipose tissue, both indicative of bone formation and confirming the results of FIGS. 2 and 3.

All patent and non-patent publications cited in this disclosure are incorporated herein to the extent as if each of those patent and non-patent publications was incorporated herein by reference in its entirety. Further, even though the disclosure herein has been described with reference to particular examples and embodiments, it is to be understood that these examples and embodiments are merely illustrative of the principles and applications of the present disclosure. It is therefore to be understood that numerous modifications may be made to the illustrative embodiments and that other arrangements may be devised without departing from the spirit and scope of the present disclosure as defined by the following claims.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. An implant configured to fit at or near a bone defect to promote bone growth, the implant comprising an oxysterol uniformly disposed in an acellular tissue matrix, wherein the acellular tissue matrix comprises porcine collagen that is particulated and has a particle size of from about 50 μm to about 500 μm and the oxysterol comprises (3S, 5S, 6S, 8R, 9S, 10R, 13S, 14S, 17S) 17-((S)-2-hydroxyoctan-2-yl)-10, 13-dimethylhexadecahydro-1H-cyclopenta[a]phenanthrene- 3, 6-diol (Oxyl33) having a particle size of from about 5 microns to about 100 microns and the Oxyl33 is in monohydrate form and in an amount of about 40 mg/cc of the matrix.

2. The implant of claim 1, wherein (i) the implant is a moldable gel, paste or putty; (ii) the implant is lyophilized; (iii) the implant is lyophilized and placed in a syringe; or (iv) the implant is hydrated and placed in a syringe.

3. The implant of claim 1, wherein the acellular tissue matrix comprises from about 5 wt. % to about 25 wt. % of acellular porcine collagen and from about 0.01 wt. % to about 90 wt. % Oxyl33.

4. The implant of claim 1, wherein the implant further comprises a fluid from about 25 wt. % to about 50 wt. % and a bone material in an amount from about 25 wt. % to about 75 wt. %.

5. The implant of claim 1, comprising a bone material having a form selected from a group consisting of
demineralized bone matrix;
mineralized bone;
demineralized bone fibers; and
demineralized bone chip.

6. The implant of claim 1, comprising a fluid having at least one component selected from a group of components consisting of water, saline, DMSO, acetic acid, acetone, DME, DMF, MTBE, acetonitrile, butanol, butanone, t-butyl alcohol, ethanol, polyethylene glycol, methanol, chlorobenzene, chloroform, toluene, propanol, pentane, heptane, ethanol, propylene glycol caprylate, diethyl ether.

7. The implant of claim 1, wherein the acellular tissue matrix is solid or semi-solid particles of collagenous material that are derived from porcine tissue material and the collagenous material preserves the original fiber architecture and molecular structure of the porcine tissue material from which it is derived, and the collagenous material is substantially free of non-fibrous tissue proteins, glycoproteins, cellular elements, lipids or lipid residues, and the collagenous material is non-cytotoxic, and the implant is capable of use as a component of a paste, gel or an injectable solution.

8. The implant of claim 1, wherein the acellular tissue matrix is a non-resorbable, substantially non-antigenic collagenous fibrous tissue preparation of porcine tissue origin, which is suitable for homo- or heterotransplantation as a permanent repair for tissue injuries, which the preparation retains the natural structure and original architecture of the porcine tissue, is substantially free of non-fibrous tissue proteins and glycoproteins, is substantially free of cellular elements, is substantially free of lipids and lipid residues and is non-cytotoxic, wherein the preparation is capable when implanted of being recolonized by host cells.

9. The implant of claim 1, wherein the implant is configured to be lyophilized and then rehydrated before implantation at or near a bone defect.

10. The implant of claim 1, comprising a bone material having a particle size from about 125 μm to about 750 μm.

11. The implant of claim 1, wherein:
the acellular tissue matrix is solid or semi-solid particles of collagenous material that are derived from porcine tissue material; and
the collagenous material preserves the original fiber architecture and molecular structure of the porcine tissue material from which it is derived.

12. An implant configured to fit at or near a bone defect to promote bone growth, the implant comprising an oxysterol uniformly disposed in an acellular tissue matrix, wherein the acellular tissue matrix comprises porcine collagen that is particulated and has a particle size of from about 50 μm to about 500 μm and the oxysterol comprises (3S, 5S, 6S, 8R, 9S, 10R, 13S, 14S, 17S) 17-((S)-2-hydroxyoctan-2-yl)-10, 13-dimethylhexadecahydro-1H-cyclopenta[a]phenanthrene-3, 6-diol (Oxyl33) and the Oxyl33 is in monohydrate form and in an amount of about 80 mg/cc of the matrix.

13. The implant of claim 1, wherein the implant further comprises a coating of a plasticizer, the coating having a thickness in the range from about 5 microns to about 250 microns to delay the release of Oxyl33 from the implant.

14. The implant of claim 1, wherein the acellular tissue matrix further comprises about 20 mg/cc sodium carboxymethylcellulose (CMC).

15. The implant of claim 1, wherein the acellular tissue matrix comprises about 20 wt. % to about 99 wt. % of Oxyl33.

* * * * *